(12) United States Patent
Felt et al.

(10) Patent No.: US 7,320,709 B2
(45) Date of Patent: *Jan. 22, 2008

(54) METHOD AND SYSTEM FOR MAMMALIAN JOINT RESURFACING

(75) Inventors: Jeffrey C. Felt, Greenwood, MN (US); Mark A. Rydell, Golden Valley, MN (US); Paul J. Buscemi, Long Lake, MN (US); Alexander Arsenyev, Eagan, MN (US); Christopher H. Porter, Woodinville, WA (US)

(73) Assignee: Advanced Bio Surfaces, Inc., Minnetonka, MN (US)

( * ) Notice: Subject to any disclaimer, the term of this patent is extended or adjusted under 35 U.S.C. 154(b) by 116 days.

This patent is subject to a terminal disclaimer.

(21) Appl. No.: 10/722,019

(22) Filed: Nov. 24, 2003

(65) Prior Publication Data

US 2004/0107000 A1  Jun. 3, 2004

Related U.S. Application Data

(63) Continuation of application No. 10/167,963, filed on Jun. 12, 2002, now Pat. No. 6,652,587, which is a continuation-in-part of application No. 10/121,455, filed on Apr. 12, 2002, now abandoned, which is a continuation-in-part of application No. 10/098,601, filed on Mar. 15, 2002, now abandoned, which is a continuation of application No. PCT/US01/41908, filed on Aug. 28, 2001.

(60) Provisional application No. 60/228,444, filed on Aug. 28, 2000.

(51) Int. Cl.
*A61F 2/38* (2006.01)
*A61F 2/28* (2006.01)

(52) U.S. Cl. ............ 623/20.16; 623/20.32

(58) Field of Classification Search ........... 623/20.14, 623/20.16, 20.32, 20.33, 23.51, 23.58, 23.61, 623/20.15, 23.53
See application file for complete search history.

(56) References Cited

U.S. PATENT DOCUMENTS 3,030,951 A  4/1962  Mandarino (Continued)

FOREIGN PATENT DOCUMENTS

DE  4339895  3/1995

(Continued)

OTHER PUBLICATIONS

Andersson et al., "MacIntosh Arthroplasty in Rheumatoid Arthritis", *Acta Orthop.*, 1974, 45:245-259.

(Continued)

*Primary Examiner*—Pedro Philogene
(74) *Attorney, Agent, or Firm*—Fredrikson & Byron , P.A.

(57) ABSTRACT

A method and system for the creation or modification of the wear surface of orthopedic joints, involving the preparation and use of one or more partially or fully preformed and procured components, adapted for insertion and placement into the body and at the joint site. In a preferred embodiment, component(s) can be partially cured and generally formed ex vivo and further and further formed in vivo at the joint site to enhance conformance and improve long term performance. In another embodiment, a preformed balloon or composite material can be inserted into the joint site and filled with a flowable biomaterial in situ to conform to the joint site. In yet another embodiment, the preformed component(s) can be fully cured and formed ex vivo and optionally further fitted and secured at the joint site. Preformed components can be sufficiently pliant to permit insertion through a minimally invasive portal, yet resilient enough to substantially assume, or tend towards, the desired form in vivo with additional forming there as needed.

24 Claims, 13 Drawing Sheets

U.S. PATENT DOCUMENTS

| | | | |
|---|---|---|---|
| 3,728,742 A | 4/1973 | Averill et al. | |
| 3,815,599 A | 6/1974 | Deyerle | |
| 4,081,866 A | 4/1978 | Upshaw | |
| 4,203,444 A | 5/1980 | Bonnell et al. | |
| 4,456,745 A | 6/1984 | Rajan | |
| 4,463,141 A | 7/1984 | Robinson | |
| 4,477,604 A | 10/1984 | Oechsle, III | |
| 4,502,161 A | 3/1985 | Wall | |
| 4,647,643 A | 3/1987 | Zdrahala | |
| 4,651,736 A | 3/1987 | Sanders | |
| 4,722,948 A | 2/1988 | Sanderson | |
| 4,743,632 A | 5/1988 | Marinovic et al. | |
| 4,772,287 A | 9/1988 | Ray et al. | |
| 4,808,691 A | 2/1989 | König et al. | |
| 4,873,308 A | 10/1989 | Coury et al. | |
| 4,880,610 A | 11/1989 | Constanz | |
| 4,969,888 A | 11/1990 | Scholten et al. | |
| 5,007,940 A | 4/1991 | Berg | |
| 5,067,964 A | 11/1991 | Richmond et al. | |
| 5,082,803 A | 1/1992 | Sumita | |
| 5,108,404 A | 4/1992 | Scholten et al. | |
| 5,109,077 A | 4/1992 | Wick | |
| 5,143,942 A | 9/1992 | Brown | |
| 5,166,115 A | 11/1992 | Brown | |
| 5,254,662 A | 10/1993 | Szycher et al. | |
| 5,278,201 A | 1/1994 | Dunn et al. | |
| 5,344,458 A * | 9/1994 | Bonutti | 623/20.32 |
| 5,344,459 A | 9/1994 | Swartz | |
| 5,509,934 A | 4/1996 | Cohen | |
| 5,525,418 A | 6/1996 | Hashimoto et al. | |
| 5,549,683 A * | 8/1996 | Bonutti | 623/20.33 |
| 5,556,429 A | 9/1996 | Felt | |
| 5,624,463 A | 4/1997 | Stone et al. | |
| 5,725,531 A | 3/1998 | Shapiro | |
| 5,795,353 A | 8/1998 | Felt | |
| 5,888,220 A | 3/1999 | Felt et al. | |
| 5,944,759 A * | 8/1999 | Link | 623/18.11 |
| 6,048,345 A | 4/2000 | Berke et al. | |
| 6,079,868 A | 6/2000 | Rydell et al. | |
| 6,140,452 A | 10/2000 | Felt et al. | |
| 6,206,927 B1 * | 3/2001 | Fell et al. | 623/20.29 |
| 6,224,630 B1 | 5/2001 | Bao et al. | |
| 6,248,131 B1 | 6/2001 | Felt et al. | |
| 6,558,421 B1 | 5/2003 | Fell et al. | |
| 6,855,165 B2 * | 2/2005 | Fell et al. | 623/14.12 |
| 2001/0037114 A1 | 11/2001 | Dinger et al. | |
| 2003/0055500 A1 | 3/2003 | Fell et al. | |
| 2003/0055501 A1 | 3/2003 | Fell et al. | |
| 2003/0060882 A1 | 3/2003 | Fell et al. | |
| 2003/0060883 A1 | 3/2003 | Fell et al. | |
| 2003/0060884 A1 | 3/2003 | Fell et al. | |
| 2003/0060885 A1 | 3/2003 | Fell et al. | |
| 2003/0060888 A1 | 3/2003 | Fell et al. | |
| 2004/0006393 A1 | 1/2004 | Burkinshaw | |
| 2004/0199249 A1 | 10/2004 | Fell | |
| 2004/0199250 A1 | 10/2004 | Fell | |
| 2005/0033424 A1 | 2/2005 | Fell | |

FOREIGN PATENT DOCUMENTS

| | | |
|---|---|---|
| DE | 19823325 | 3/2000 |
| EP | 0 353 936 | 2/1990 |
| EP | 0 378 002 | 7/1990 |
| EP | 0 505 634 | 9/1992 |
| EP | 0 521 573 | 1/1993 |
| FR | 2 639 823 | 12/1988 |
| WO | WO 93/11723 | 6/1993 |
| WO | WO 95/30388 | 11/1995 |
| WO | WO 95/31946 | 11/1995 |
| WO | WO 95/31948 | 11/1995 |
| WO | WO 97/26847 | 7/1997 |
| WO | WO 98/20939 | 5/1998 |
| WO | WO 99/44509 | 9/1999 |
| WO | WO 99/61084 | 12/1999 |
| WO | WO 00/59411 | 10/2000 |
| WO | WO 01/066021 | 9/2001 |

OTHER PUBLICATIONS

Cameron et al., "Review of a Failed Knee Replacement and Some Observations on the Design of a Knee Resurfacing Prosthesis", *Archives of Orthopaedic and Traumatic Surgery*, 1980, pp. 87-89.

Clary et al., "Experience with the MacIntosh Knee Prosthesis", *So. Medical Journal*, vol. 65, No. 3, Mar. 1972, pp. 265-272.

Conaty et al., "Surgery of the Hip and Knee in Patients with Rheumatoid Arthritis", *J. Bone and Joint Surgery*, vol. 55, No. 2, Mar. 1973, pp. 301-314.

Emerson et al., "The Use of the McKeever Metallic Hemiarthroplasty for Unicompartmental Arthritis", *J. Bone and Joint Surgery*, vol. 67 No. 2, Feb. 1985, pp. 208-212.

Hastings et al., "Double Hemiarthroplasty of the Knee in Rheumatoid Arthritis", *J. Bone and Joint Surgery*, vol. 55, No. 1, Feb. 1973, pp. 112-118.

Jessop et al., "Follow-up of the MacIntosh Arthroplasty of the Knee Joint", *Rheum. Phys. Med.*, vol. 11, 1972, pp. 217-224.

Kay et al., "The MacIntosh Tibial Plateau Hemiprosthesis for the Rheumatoid Knee", *J. Bone and Joint Surgery*, vol. 54, No. 2, May 1972, pp. 256-262.

Kozinn et al., "Surgical Treatment of Unicompartmental Degenerative Arthritis of the Knee", *Orthopedic Surgery and Degenerative Arthritis*, vol. 14, No. 3, Dec. 1988, pp. 545-564.

MacIntosh et al., " The Use of the Hemiarthroplasty Prosthesis for Advanced Osteoarthritis and Rheumatoid Arthritis of the Knee", *J. Bone and Joint Surgery*, vol. 54, No. 2, May 1972, pp. 244-255.

McKeever, "Tibial Plateau Prosthesis", *Clinical Orthopaedics and Related Research*, No. 192, 1985, pp. 3-12.

Porter et al., "MacIntosh arthroplasty: a long-term review", *J.R. Coll. Surg. Edinb.*, vol. 33, Aug. 1988, pp. 199-201.

Potter et al., "Arthroplasty of the Knee in Rheumatoid Arthritis and Osteoarthritis", *J. Bone and Joint Surgery*, Vo. 54, No. 1, Jan. 1972, pp. 1-24.

Potter, "Arthroplasty of the Knee with Tibial Metallic Implants of the McKeever and MacIntosh Design", *Surgical Clinics of North America*, No. 49, No. 4, Aug. 1969, pp. 903-915.

Sbarbaro, "Hemi-tibial plateau prosthesis ten years experience in 500 knee arthroplasties", *Acta Orthopaedica Belgica*, vol. 39., 1973, pp. 91-100.

Schorn et al., "MacIntosh Arthroplasty in Rheumatoid Arthritis", *Rheumatology and Rehabilitation*, 1978, 17:155-163.

Scott et al., "McKeever Metallic Hemiarthroplasty of the Knee in Unicompartmental Degenerative Arthritis", *J. Bone and Joint Surgery*, vol. 67, No. 2., Feb. 1985, pp. 203-212.

Stauffer et al., "The MacIntosh Prosthesis", *Arch Surg.*, vol. 110, Jun. 1975, pp. 717-720.

Swanson et al., "Unicompartmental and Bicompartmental Arthroplasty of the Knee with a Finned Metal Tibial-Plateau Implant", *J. Bone and Joint Surgery*, 1985, pp. 1175-1182.

Taylor et al., "MacIntosh arthroplasty in rheumatoid arthritis", "Proceedings and Reports of Universities, Colleges, Councils and Associations", *J. Bone and Joint Surgery*, vol. 48, No. 1, Feb. 1966, pp. 119-120.

Wayne, "Use of the McIntosh Prosthesis in Surgical Reconstruction of the Knee", Abstracts of 1971 Proceedings, *J. Bone and Joint Surgery*, Jun. 1972, pp. 292-293.

Wordsworth et al., "MacIntosh arthroplasty for the rheumatoid knee: 10-year follow up", *Annals of the Rheumatic Diseases*, 1985, 44:738-741.

McCollum et al., "Tibial Plateau Prosthesis in Arthroplasty of the Knee", *J. Bone and Joint Surgery*, vol. 52, No. 4, Jun. 1970, pp. 827-828.

* cited by examiner

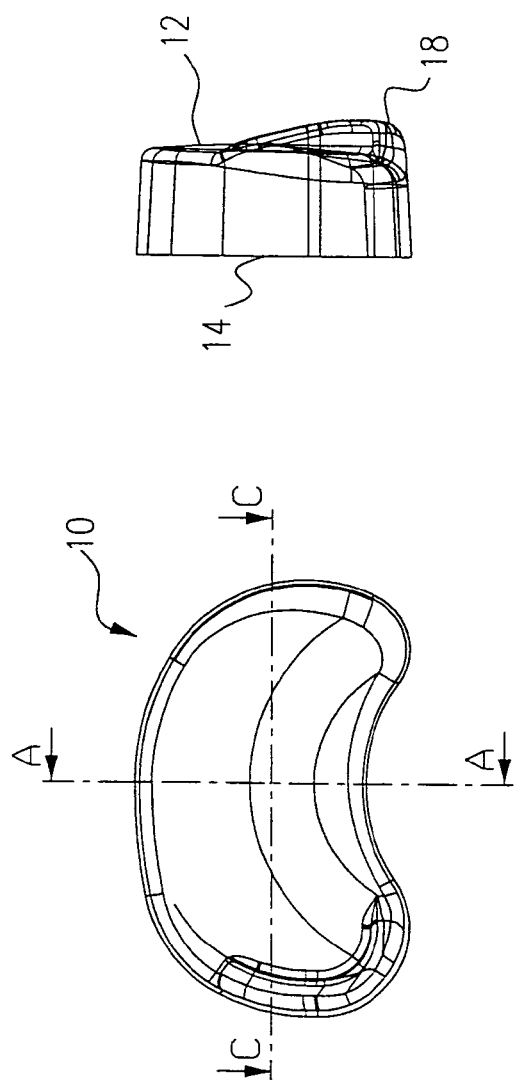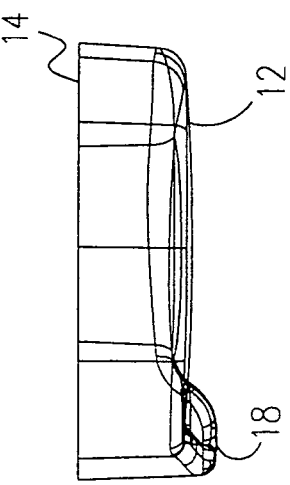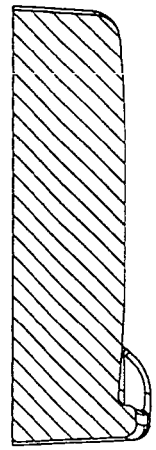
FIG. 12(D) SECTION A-A
FIG. 12(E) SECTION C-C
FIG. 12(C)
FIG. 12(A)
FIG. 12(B)
FIG. 12

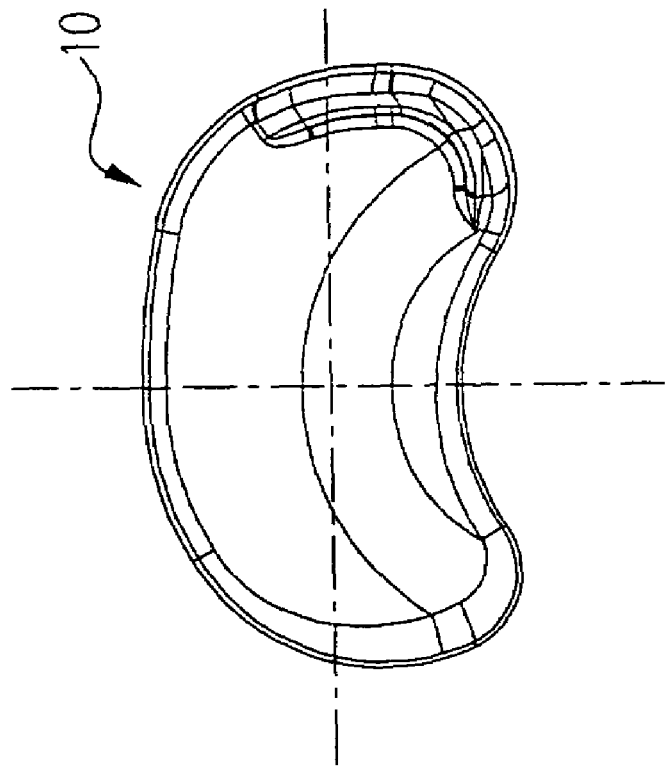
FIG. 13(A)
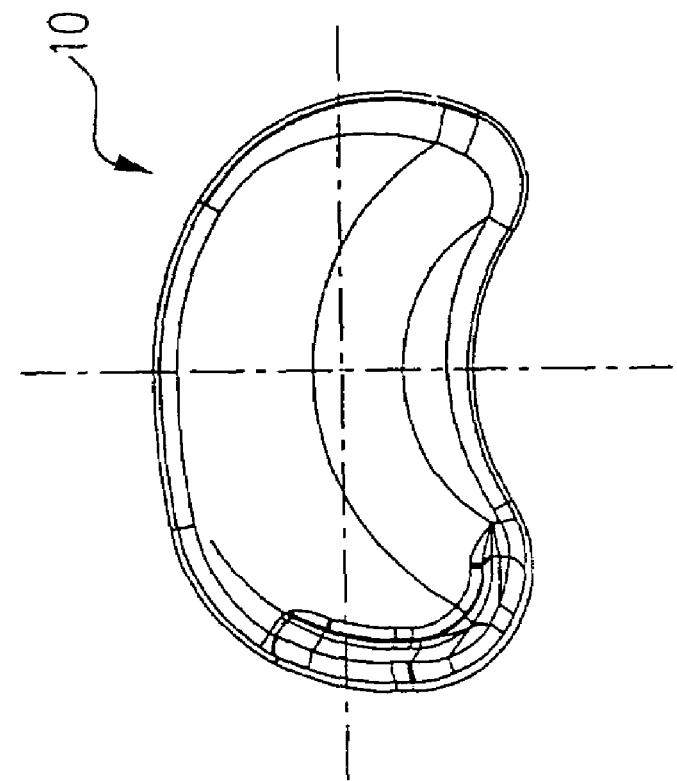
FIG. 13(B)
FIG. 13

METHOD AND SYSTEM FOR MAMMALIAN JOINT RESURFACING

CROSS REFERENCE TO RELATED APPLICATIONS

The present application is a continuation of U.S. application Ser. No. 10/167,963 filed Jun. 12, 2002 now U.S. Pat. No. 6,652,587, which is a continuation-in-part of U.S. application filed Apr. 12, 2002 and assigned U.S. Ser. No. 10/121,455 now abandoned, which is a continuation-in-part of US application filed Mar. 15, 2002 and assigned U.S. Ser. No. 10/098,601, which is a continuation of an international patent application filed Aug. 28, 2001 and assigned Ser. No. PCT/US01/41908 which itself is a continuation-in-part of Provisional U.S. Application Ser. No. 60/228,444, filed Aug. 28, 2000, the entire disclosures of which are incorporated herein by reference.

TECHNICAL FIELD

In one aspect, this invention relates to biomaterials formed ex vivo for implantation and use within the body. In another aspect, the invention relates to in situ curable biomaterials. In yet another aspect, this invention further relates to the field of orthopedic implants and prostheses, and more particularly, for implantable materials for use in orthopedic joints.

BACKGROUND OF THE INVENTION

Applicant has previously described, inter alia, prosthetic implants formed of biomaterials that can be delivered and finally cured in situ, e.g., using minimally invasive techniques. See for instance, U.S. Pat. Nos. 5,556,429, 5,795,353, 5,888,220, 6,079,868, 6,140,452, 6,224,630 and 6,248,131 as well as published International Application Nos. WO 95/30388 and WO 97/26847 and International Application PCT/US97/20874 filed Nov. 14, 1997 (the disclosures of each of which are incorporated herein by reference). Certain of these applications describe, inter alia, the formation of a prosthetic nucleus within an intervertebral disc by a method that includes, for instance, the steps of inserting a collapsed mold apparatus (which in a preferred embodiment is described as a "balloon") through a cannula that is itself positioned through an opening within the annulus, and filling the balloon with a flowable biomaterial that is adapted to finally cure in situ and provide a permanent disc replacement. See also, Applicant's "Porous Biomaterial and Biopolymer Resurfacing System" (PCT/US99/10004), as well as "Implantable Tissue Repair Device (PCT/US99/11740), and "Static Mixer" (PCT/US99/04407) applications.

See also, U.S. Pat. No. 3,030,951 (Mandarino), U.S. Pat. No. 4,203,444 (Bonnell et al.), U.S. Pat. No. 4,456,745 (Rajan), U.S. Pat. No. 4,463,141 (Robinson), U.S. Pat. No. 4,476,293 (Robinson), U.S. Pat. No. 4,477,604 (Oechsle, III), U 4,647,643 (Zdrahala), U.S. Pat. No. 4,651,736 (Sanders), U.S. Pat. No. 4,722,948 (Sanderson), U.S. Pat. No. 4,743,632 (Marinovic et al.) 4,772,287 (Ray et al.), U.S. Pat. No. 4,808,691 (Konig et al.), U.S. Pat. No. 4,880,610 (Constanz), U.S. Pat. No. 4,873,308 (Coury et (Scholten et al.), U.S. Pat. No. 5,007,940 (Berg), U.S. Pat. No. 5,067,964 (Richmond et al.), U.S. Pat. No. 5,082,803 (Sumita), U.S. Pat. No. 5,108,404 (Scholten et al.), U.S. Pat. No. 5,109,077 (Wick), U.S. Pat. No. 5,143,942 (Brown), U.S. Pat. No. 5,166,115 (Brown), U.S. Pat. No. 5,254,662 (Szycher et al.), U.S. Pat. No. 5,278,201 (Dunn et al.), U.S. Pat. No. 5,525,418 (Hashimoto et al.), U.S. Pat. No. 5,624,463 (Stone et al.), U.S. Pat. No. 6,206,927 (Fell), and EP 0 353 936 (Cedar Surgical), EP 0 505 634 A1 (Kyocera Corporation), EP 0 521 573 (Industrial Res.), and FR 2 639 823 (Garcia), WO 93/11723 (Regen Corporation), WO 9531946 (Milner), WO 9531948 (Kuslich).

Applicant's PCT Application No. PCT/US97/00457 (WO 9726847A1) includes the optional use of a mold, such as a balloon, and describes the manner in which "[t]he mold created within the joint is preferably of sufficient shape and dimensions to allow the resulting cured biomaterial to replace or mimic the structure and function of the removed fibrocartilage. The mold can be formed of synthetic and/or natural materials, including those that are provided exogenously and those provided by the remaining natural tissues. The mold can either be removed from the site, upon curing of the biomaterial, or is sufficiently biocompatible to allow it to remain in position."

Applicant's later PCT Application No. PCT/US97/20874 (WO 9820939A2) further describes the manner in which "'mold' will refer to the portion or portions of an apparatus of the invention used to receive, constrain, shape and/or retain a flowable biomaterial in the course of delivering and curing the biomaterial in situ. A mold may include or rely upon natural tissues (such as the annular shell of an intervertebral disc) for at least a portion of its structure, conformation or function. The mold, in turn, is responsible, at least in part, for determining the position and final dimensions of the cured prosthetic implant. As such, its dimensions and other physical characteristics can be predetermined to provide an optimal combination of such properties as the ability to be delivered to a site using minimally invasive means, filled with biomaterial, and optionally, then remain in place as or at the interface between cured biomaterial and natural tissue. In a particularly preferred embodiment the mold material can itself become integral to the body of the cured biomaterial."

Applicant's own use of such mold apparatuses to date has concentrated largely on the use of thin, extensible balloons adapted to be positioned and then filled in situ with curable biomaterial, with particular use as a replacement for the intervertebral disc following microdiscetomy. In turn, there has been considerably less focus, to date, on the use of any such molds in other joints, such as the knee. FIGS. 6 and 7 of Applicant's PCT Publication No. WO 920939 A2, for instance, shows a balloon and corresponding drilling template for use in knee surgery, the balloon having foot portions protruding from a generally ovoid inflatable portion.

Finally, U.S. Pat. No. 6,206,927 describes a self-centering meniscal prosthesis device suitable for minimally invasive, surgical implantation into the cavity between a femoral condyle and the corresponding tibial plateau is composed of a hard, high modulus material shaped such that the contour of the device and the natural articulation of the knee exerts a restoring force on the free-floating device. In what appears to be a related manner, Sulzer has introduced a unicompartmental interpositional spacer to treat osteoarthritis in the knee. See "Little Device Could Pack a Big Punch", Sulzer Medica Journal Edition 2/2000 (www.sulzermedica.com/media/smj-full-tex/2000/0002-full-text-6.html). The device is described as a metallic kidney-shaped insert which fills in for the damaged cartilage between the femur and the tibia.

Such a metallic device, as described in either the Fell patent and/or Sulzer's product literature, is described as appropriate for use in younger patients with moderate to severe chondromalacia, particularly since the product provides a hard, self-centering meniscal device that is "devoid of physical means that fix its location". In so doing, the device of Fell et al. tends to require a significant amount of intact cartilage and meniscus. Applicant's own products to date, including those improved embodiments described herein, have been largely geared toward more elderly patients, where such healthy cartilage is lacking. In turn, Applicant's devices tend to provide angular correction and improved anchoring of the implant at the joint surface.

The recently issued Search Report in parent application PCT/US01/41908 includes two references, namely DE 19823325C1 and DE 4339895 C1 directed to multipart devices that include portions mechanically affixed to bone, and in turn, are unrelated to a polymeric interpositional device of the type presently claimed.

In spite of developments to date, there remains a need for a joint prosthesis system that provides an optimal combination of properties such as ease of preparation and use, and performance within the body.

BRIEF DESCRIPTION OF THE DRAWING

In the Drawing:

FIGS. 12 and 13 show various views of a particularly preferred knee implant of the present invention, including top plan view 12a, front plan view 12b, side plan view 12c, section view 12d across A-A, and section view 12e across C-C, as well as top plan views of implants 13a and 13b for the left and right knees, respectively.

SUMMARY OF THE INVENTION

Figure 1A:
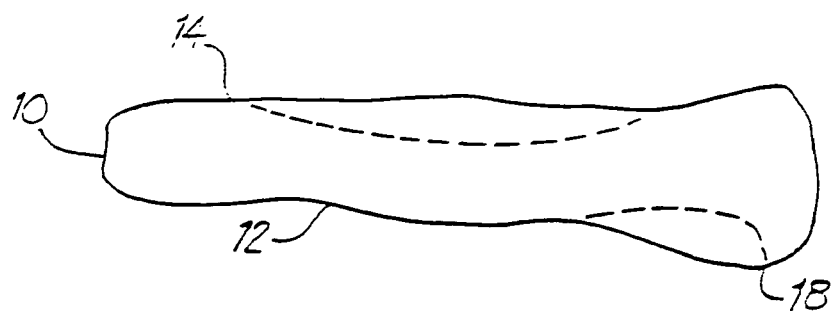
FIG. 1 shows top and side perspectives (FIGS. 1a and 1b, respectively) of a preferred preformed knee implant prepared according to the present invention.

The present invention provides a method and system for the creation or modification of the wear surface of orthopedic joints, including one or both of two articulating surfaces and/or portions thereof, and particularly articulating joints such as the knee. In one preferred embodiment, the method relies, at least in part, upon the manner in which the various stages of curing a curable biomaterial, and in turn, the various stages of forming a component from the cured or curing biomaterial, can be correlated and optimized in a desired manner. In turn, such a method provides the ability to both generally and specifically form the component for use in situ.

The present invention includes a variety of embodiments, each of which preferably includes one or more components that are formed ex vivo, and that are adapted to be inserted and finally formed or assembled in situ in order to provide a final prosthesis and articulating joint surface. Examples of the various embodiments include, for instance, 1) one or more components that are each at least partially, and optionally completely, molded ex vivo, in a manner that permits the component to be inserted, and optionally finally formed, in situ, 2) a plurality of preformed components adapted to be assembled in situ, for instance in an overlapping or interlocking fashion, 3) an insertable open (e.g., saucer shaped) mold, adapted to be inserted and positioned within the joint site, and there used in combination with a flowable biomaterial adapted to be delivered to the open mold in situ, under conditions that permit the flowable biomaterial to cure in contact and/or combination with the mold in order to form a final prosthesis, 4) one or more generally extensible envelope (e.g., balloon-type) molds, adapted to be positioned and filled in situ with corresponding curable biomaterials, one or more of the molds themselves providing one or more regions of generally non-extensible, preformed material. In one embodiment, for instance, a plurality of such envelope portions (e.g., a bi-compartmental single envelope) can be adapted for use on both the medial and lateral tibial surfaces, respectively.

By the selection and use of a suitable biomaterial, and other features as described herein, the present invention provides an optimal combination of benefits, as compared to methods previously described. Such benefits include those that arise in the course of preparation and storage (e.g., sterility, storage stability), those that arise in the surgical field itself (e.g., ease of use, adaptability, predictability), and those that arise in the course of long term use within the body (e.g., biocompatibility, moisture cure characteristics, tissue congruity and conformability, retention, wear characteristics, and physical-mechanical properties).

In one preferred embodiment, the method and system involve the preparation and use of partially or completely cured components that can be formed outside the body, for insertion and placement into the body, and that can then be further formed within the joint site in order to enhance conformance. The optional ability to finally form one or more components in situ provides various additional benefits, such as increased control over the overall size and shape of the final prosthesis, improved shape and compliance of the surface apposing natural bone, and finally, improved shape and compliance of the opposite, articulating surface. The method and system permit the on site preparation or previous manufacture of a unicompartmental interpositional arthroplasty device from polymeric materials such as polyurethane.

In a related and particularly preferred embodiment, the implant can be prepared (including full cured) ex vivo, for later implantation. In a particularly preferred embodiment, as described below, the present invention therefore provides an implant that is designed to be formed to and congruent with the tibial surface, having a final femoral surface shape that serves largely as a glide path with respect to the femoral condyle. Such a device can be used in patients having joints that have progressed to the stage of "bone on bone", and thus provides a replacement for the function of articular cartilage as well as meniscus, and particularly at the central weight-bearing area, in order to restore alignment, providing an elastomeric, cushioning function. A preferred implant of this type is also congruent with the tibial surface, based upon both its initial shape, together with whatever final shaping may occur in situ. In turn, the present implant is more permanently anchored in place, in significant part by one or more posterior projections, such as the posterior lip shown in FIGS. 1, and 12-13 as well by the optional but preferred use of anterior fixation means (such as embedded sutures).

As shown in those Figures, such an embodiment includes a unique combination of a femoral glide path and convexity of the tibial surface of the implant, together with a posterior mesial lip. In turn, as provided in the Figures and related description, the implant provides an indentation adapted to accommodate the tibial spine, which together with a slight feathering of the implant on the underside at the tibial spine, the general kidney shape of the implant, and the convexity of the tibial surface, will permit the implant to be congruent with the concave tibia and the posterior mesial lip that extends over the posterior portion of the tibia and into the mesial side of the tibia into the PCL fossa of the tibia. Importantly, such an implant can be provided in various sizes to accommodate different anterior-posterior dimensions of the tibia and different tibial concavities. In other words, the amount of convexity of the tibial surface will be varied with the different sizes depending on the amount of actual concavity that there is in the tibia.

As used herein, the word "cure", and inflections thereof, will refer to the extent to which a curable biomaterial, as used to form a component of this invention, has begun or completed whatever physical-chemical reactions may be contemplated in the course of fully forming the component, prior to or at the surgical site, for long term use in situ. In turn, the biomaterial can be considered as uncured (as in component parts that have not yet been mixed or compositions that have not yet been activated), or it can be partially cured (e.g., wherein the components have been mixed, or compositions activated, under conditions suitable to begin the curing process), or it can be fully cured (e.g., in which case, whatever chemical reactions may have occurred have substantially subsided). Generally, uncured compositions are sterile, storage stable, and often flowable, though are typically not yet formed or capable of being formed.

Curing compositions, by contrast, generally begin as flowable compositions, but become nonflowable over a finite time period as they begin to gel or set. Curing compositions can also be minimally formed, e.g., outside the body by the use of molds and/or suitable shaping tools, and/or within the body, as by the initial positioning of the component on supporting bone and by the repositioning of opposing, articulating bone surfaces. Thereafter, it is contemplated and possible that some compositions of this invention can be further formed, over time, as by the gradual effect of articulating bone in the course of long term use.

As also used herein, the word "form", and inflections and variations thereof, will refer to the manner and extent to which a component has been sized and shaped, in either a general and/or specific manner, for use at a joint site. In turn, the forming of such a component can occur either ex vivo and/or in vivo, as well as in a general manner (e.g., by the use of an ex vivo mold or tools) and/or a specific manner (e.g., by final curing in apposition to supporting bone and/or opposing articulating bone surfaces), as well as combinations thereof.

A component can be "specifically" formed in this manner in order to conform the component (and particularly its surfaces) to the corresponding specific shapes and dimensions of bone in situ, including both supporting bone surfaces and/or opposing (e.g., articulating) bone surfaces. Such specific conformation, in turn, can be used to improve a variety of characteristics of the final implant, including comfort, mechanical performance, and/or long term stability. Such conformation can also include aspects in which one or more components, or the composite prosthesis, are "conformed" in correspondence with the joint site (e.g., by final shaping and curing processes that occur in situ).

Such conformation can also include aspects in which the components, or prosthesis itself, are adapted to be "deformed" within the site, as by the application of force. For instance, a substantially fully formed component can be provided to have sufficient mechanical properties (e.g., strength and resilience) to permit it to be inserted into a joint site and effectively deformed under normal anatomic forces For instance, a substantially convex component can be deformed to assume the corresponding concave shape in situ, in, while retaining sufficient resilient strength to tend towards its original convex shape (e.g., analogous to the manner in which a locking washer can be deformed in use, while tending toward its original shape). Preferably, a final knee component is adapted to be deformed under conditions of use within the body (e.g., under physiologic load), while maintaining desired size and tibial congruency, and in a manner that provides desired fit and thickness for desired angular correction.

Hence a "preformed" component will generally refer to a component that is at least partially formed ex vivo, as by the surgeon's selection and use of an appropriately sized ex vivo mold. Such a preformed component can be specifically formed as well, including in an ex vivo fashion, as by the use of a customized mold that is itself reflective of the particular dimensions and contours of the intended joint site. Such customized molds can be prepared, for instance, by the use of external imaging means, and/or by the appropriate use of negative and/or positive molds taken at the tissue site. Optionally, and preferably, the preformed component is specifically formed, in whole or in part, by being positioned in situ, prior to the completion of the curing process, and in apposition to both supporting bone and opposing bone surfaces. Once positioned within the joint site, any such component or prosthesis can be adapted to be deformed in order to improve its retention and/or performance in situ, e.g., resiliently deformed upon release of distracting forces and repositioning of the opposing bone surface.

For instance, a preformed composition is provided, formed initially by the ex vivo onset of cure, in which the composition can be implanted within on the order of 10 seconds to several days of the onset of cure, preferably within about 30 seconds to about 10 minutes, and more preferably within about one to about five minutes, while maintaining a surface exotherm of less than about 50C, and more preferably less than about 45C once positioned within the body.

Once positioned in vivo, optional preferred preformed components of this invention are adapted to be finally shaped, for a period of between about 10 seconds and one or more hours, and more preferably between about one minute and about five minutes. The lower limit is defined largely by the time it takes to effectively reposition bone, or otherwise re-establish suitable force on the implant. The upper limit, in turn, is generally defined by the susceptibility of the implanted composition to further deformation or shaping. Such final shaping is generally accomplished, at least in part, under the force brought about by repositioning articulating bone surfaces. In one preferred embodiment, the partially cured composition is implanted under conditions that permit it to deform less than about 15%, preferably less than about 10%, and most preferably less than about 5%, under physiologic forces, while maintaining tibial congruency and imparting desired angular correction.

Hence, a particularly preferred preformed component of this invention can be implanted within an initial about one to about five minutes of the onset of its formation, and once implanted can be further molded or formed for a further period of about one to about five additional minutes, in a manner that permits the resultant implant to substantially retain a desired final form and function.

The system of the present invention thereby provides the surgeon with a variety of options, based on the manner in which these curing and forming processes are correlated. In one particularly preferred embodiment, for instance, the surgeon is provided with a composition adapted to be partially cured and generally formed ex vivo, and then promptly inserted into the body and positioned at the joint site, where it can be finally, and specifically, formed in the course of becoming fully cured.

By partially or fully curing the prosthesis ex vivo, the present system simplifies the preparation process considerably, e.g., by lessening or avoiding potential problems (such as curing in the presence of moisture, and surface exotherm in the presence of tissue) that can arise when a comparable composition is mixed and delivered to the joint site while it is still flowable. Surprisingly, the present system permits such prostheses to be not only formed, but also manipulated and inserted into the joint (e.g., through an incision of between about 1 cm and about 3 cm). Once inserted, the prosthesis can be positioned, and further formed in situ, all within a reasonable time frame. In fact, it has been found that the procedure is amenable to outpatient use and even regional anesthesia.

Moreover, the present system can avoid the use of such processes as the drilling anchor holes into the underlying bone, distraction of the knee joint, ligament release, leveling of the tibial plateau, and the various other procedures typically involved with delivering the biomaterial directly to the joint site in still flowable form. Yet, the prosthesis of the present invention provides a combination of properties such as the extent of congruence with underlying bone, wear characteristics, fracture toughness, and avoidance of fibrillated articular cartilage, that meets or exceeds the combination of properties obtained using a comparable biomaterial in flowable form, delivered and largely cured in situ.

In addition to its immediate use in such joints as the knee, the system of the present invention provides particular advantages when applied to ball and socket joints, such as the hip. In one such embodiment, a balloon can be filled with a biomaterial as described herein, and inserted and positioned within the acetabulum, prior to or following filling, to provide a soft, conformable, durable lining for the placement of a hip prosthetic portion. In a further embodiment, the method and system involve the preparation and use of one or more partially or fully cured component(s) formed outside the body, for insertion and placement into the body and optionally further fitting and securing at the joint site. These preformed component(s) typically require less manipulation at the bedside and allow for alternative methods of terminal sterilization, and final inspection and release at the manufacturing site.

In a particularly preferred embodiment, the present invention therefore provides an implant that is designed to be formed to and congruent with the tibial surface, having a final femoral surface shape that serves largely as a glide path with respect to the femoral condyle.

This can be compared to other devices, such as that of the '927 patent described above, which discloses a "self centering" device, formed entirely outside the body, and generally of a hard metal, by first determining the geometry of the entire knee compartment, including both the femoral and tibial surfaces. The device is designed to be very hard, and based on such things as the concavity and convexity of various surfaces, which are designed to permit continued movement (translational and rotational) and re-positioning of the device within the knee compartment in the course of use. In turn, the device is permitted and expected to continually move within the joint over the course of its use.

The present device can be used in patients having joints that have progressed to the stage of "bone on bone", and thus provides a replacement for the function of articular cartilage as well as meniscus, and particularly at the central weight-bearing area, in order to restore alignment.

The implant provides an elastomeric, cushioning function, as compared to the rigid and hard device of the '927 patent. The present implant is also congruent with the tibial surface, based upon both its initial shape and the final shaping that occurs in situ. In turn, the present implant is more permanently anchored in place, in significant part by the posterior lip shown in FIGS. 1, and 12-13 as well by the use of anterior fixation means (such as embedded sutures).

Finally, the presently preferred implant has a peripheral thickness that is generally thinner than the thickness of their central portion, and is positioned only partially within the knee compartment as defined in the '927 patent, having a posterior lip that extends well beyond a compartment defined in that manner, and that serves a key role in fixation.

DETAILED DESCRIPTION

The method and system (e.g., preformed component(s) and/or curable biomaterial and mold) can be used to prepare a final prosthesis, in vivo, that provides a first major surface in apposition to and retained upon the supporting bone itself, and a second (generally substantially parallel and opposite) major surface adapted to provide a wear surface for opposing (e.g., articulating) bone. By "retained upon" it is meant that the final prosthesis is maintained in a desired position upon the supporting bone surface in a manner suitable for its intended use, e.g., by the use of one or more anchor points, by the use of adhesive or other suitable interface materials, by the use of sutures, staples, and the like, and/or by a mechanical lock achieved by the combination of a bone-contacting surface suitably conformed or conformable to the terrain of supporting bone, together with the retaining (and optionally including deforming) effect achieved upon repositioning opposing articulating bone surface.

The first and second major surfaces can be provided in any suitable manner, for instance, 1) by the preparation and insertion of a single partially cured and generally preformed component into the joint, preferably under conditions that permit the component to become further, and specifically, formed in vivo, 2) by adding a flowable biomaterial to an initial preformed component (e.g., in the shape of a balloon or open mold) positioned at the tissue site, 3) by placing one or more fully cured and preformed components at the tissue site and optionally further fitting, adapting and/or securing the component(s) as needed, and/or 4) by assembling one or more preformed components in situ (e.g., side by side in an interlocking fashion upon the surface) such that the assembled components cooperate to provide the first and second major surfaces.

The system can therefore include modular implants, that include one or more preformed components as described herein, in combination with one or more other (e.g., metallic) components. Any or all of such components can be made using materials having "shape memory" that permits the components to be easily inserted into the joint space, in a manner that permits the component(s) to assume or recover an alternative shape upon the application of energy (e.g., heat slightly above body temperature). Optionally, such alternative shape can be achieved prior to insertion into the body. Alternatively, the molded in the body implant can be taken out and reformed (e.g., by heat, radiation or other suitable means) and reimplanted for final fit.

In addition to the partially or fully cured preformed component(s) and/or curable biomaterial and related molds, the method and system of this invention include the optional use of various additional materials and/or steps, e.g., to prepare the bone surface itself, to provide suitable interfaces (e.g., adhesive interfaces and/or protrusions that can be further secured to the joint site or by smoothing of the femoral condyle or tibial plateau as needed), to treat one or more surfaces in order to provide them with different or improved properties as compared to the inherent properties of the material providing the surface, and the like. Examples of such materials include, for instance, the use of adhesive materials, tissue in-growth stimulators, and fibrous materials (e.g., webs adapted to tether the implant and/or to facilitate fibrous tissue ingrowth).

The partially or fully cured preformed component(s) can themselves each provide uniform or non-uniform properties, and can be provided in a plurality or range of styles and sizes. These components can be designed to conform to lateral or medial compartments, or both, and to right or left knees, or both. In a preferred embodiment, all embodiments can be inserted into the joint site in a minimally invasive fashion. By "minimally invasive", in this context, it is meant that the procedure of sizing, inserting, positioning and forming the prosthesis, in situ, can preferably be accomplished without the need for open, invasive incisions of the type conventionally used for inserting total knee prostheses. In a preferred embodiment, the partially cured preformed components can be further formed and fully cured in vivo to enhance compliance with the joint site.

The surface of the partially or fully cured preformed component(s) can also be modified to provide any desired properties (e.g., promote adhesion), such as by the design and use of polymers themselves or by surface treatment of the fully cured or curing embodiments to provide suitable reactive groups such as amines, hydroxyl groups, or other reactive or hydrogen bonding functionalities. Similarly, the partially cured preformed component or fully cured component, including balloons or composite materials, can be provided with appropriate surface coatings, e.g., biologically active agents to promote desired tissue interactions, including tissue or cellular adhesion, such as those selected from the group consisting of cytokines, hydroxyapatite, collagen, and combinations thereof. Such biologically active agents can also include, for instance, anti-inflammatory agents, antitumor agents, antibiotics, complement inhibitors, cytokines, growth factors, or inhibitors of growth factors and cytokines, as well as combinations of any such biologically active agents with each other and/or with adjuvants, and the like.

In one embodiment of this invention, partially cured, and generally preformed components are inserted into the joint site, and there further and specifically formed to enhance compliance. In an alternative embodiment, fully cured components in the shape of a balloon or open mold are employed to provide a final composite material by inserting the balloon or mold into the joint and there filling it with a biomaterial that cures in situ and conforms with the joint site. In another alternative embodiment, the fully cured component(s) are provided and inserted into the joint either singly or piecemeal and optionally further fitted and secured in vivo.

As an example of the first such embodiment, the invention provides an open ex vivo mold, adapted to approximate the desired dimensions of the joint site, and to receive a curable biomaterial. A suitable mold can be formed, for instance, from the use of conventional materials such as silicone materials, that permit the curing biomaterial component to be easily and entirely removed at the desired time. Optionally, the mold can itself be provided with a coating or release liner, including those that can be integrated, in whole or in part, with the component thus formed. Once the flowable biomaterial has been delivered and partially cured in this ex vivo mold, and any optional molding or fabricating steps have occurred, the biomaterial can be removed from the mold and inserted into the joint site, under conditions suitable to permit it to be further and finally formed in vivo to enhance conformance with the joint site. Optionally, additional ex vivo forming steps or features can be performed, e.g., by imparting desired curvature and femoral glide paths, prior to inserting and final forming in vivo.

Also, in the course of molding the component ex vivo, and/or transferring it to the tissue site, various structures and/or materials can be incorporated into and/or onto the component itself, to enhance its placement, retention and/or performance in situ. For instance, the mold itself can be provided in a form sufficient to impart various integral structural features, such as tibial "tabs", adapted to provide or improve the retention of the component at the tissue site. Such tabs, for instance, can be provided in the form of one or more protrusions integral with the mold itself and adapted to be positioned within and/or affixed to the soft tissue and/or bone in vivo. Examples of such tabs are shown, for instance, in FIG. 1, where reference number 18 depicts a raised posterior portion.

An insertable component can also be provided with one or more ancillary portions or protrusions formed of materials other than that used to form the bulk of the component itself. For instance, sutures or fibrous materials can be incorporated into or onto the bulk material, for use in improving the initial and/or long term retention of the component in situ, e.g, by tethering the prosthesis at the joint site and in a desired position. Such other materials can be temporarily positioned into or upon the mold itself, for instance, or otherwise provided, in a manner that permits them to become integrated into the biomaterial as it fills the mold and becomes partially cured ex vivo. With the resulting component positioned in situ, the protrusions can be used to tether the implant, by securing them to the surrounding soft tissue and/or bone by use of adhesives, sutures, screws, pins, staples, or the like, and other types of anchors, or combinations thereof, which in turn can be prepared using bioabsorbable and/or non-bioabsorbable cements, composites, and adhesives. The materials can provide both an immediate fixation function, and optionally also a desired long term function, by permitting them to be either absorbed by the body over time, and/or to permit or encourage fibrous tissue ingrowth for long term fixation.

The reinforcing material can be provided in any suitable form, e.g., as fibers (e.g., sutures) or as a uniform woven or non-woven fabric, optionally including one or more reinforcing fibers or layers. A suitable non-woven fabric, for instance, is preferably a material such as is commercially available under the trade name Trevira Spunbond from Hoechst Celanese Corporation. The non-woven fabric is generally composed of continuous thermoplastic fiber, needle punched together to yield a felt-like fabric. In addition to fabrics like Trevira Spunbond, other materials such as polyester staple mat, glass fiber mat, as well as other organic and inorganic fiber mats and fabrics can be employed.

Reinforcing fibers can be included within the woven or non-woven fabric, or provided as separate layers of a composite. Such fiber layers can preferably include a directional reinforcing fiber layer of organic or inorganic structural reinforcing fibers such as fiberglass, carbon fibers, aramid fibers which is available from DuPont Corporation under the trade name Kevlar, linear polyethylene or polypropylene fibers such as is commercially available from Allied-Signal, Inc. (now Honeywell) under the trade name Spectra, or polyester fibers. The phrase "reinforcing fiber" can include any fiber which, when used in its own right or added to a composite fabric material, retains or enhances desired structural properties. The fibers can be randomly oriented, or preferentially, they can be oriented in one or more directions. While a number of specific types of materials have been given for use as the reinforcing fiber layer, it will be appreciated by those of ordinary skill in the art that other equivalent-type reinforcing fiber layers can be employed in the practice of the invention. A reinforcing fiber layer can be itself used to secure the prosthesis, or can be attached to a woven or non-woven fiber layer having a number of interstices or pores. Preferably, the reinforcing fiber layer and other fiber layers are secured to each other mechanically, as by conventional stitching, needle punching, stapling or buttons. In the case of certain applications, adhesives can also be used.

Similarly, a partially cured preformed component (and/or ancillary portions incorporated therein) can also be provided with suitable means to improve its ability to retain the component in situ, e.g., by the use of surface characteristics that provide improved chemical interactions with the joint site. Such interactions can be achieved by the judicious use of bulk material compositions themselves and/or the use of adhesives or other suitable interface materials. The partially cured, preformed, component can also be physically modified to increase its interactions with joint site, as by surface roughening, etching or cross-hatching, which would tend to provide increased surface area, and in turn, improved mechanical retention. A partially cured, preformed, component can also be retained by external means that are otherwise secured to the surrounding bone and/or soft tissue by use of adhesives, sutures, screws, pins, staples or the like or combinations thereof. On the major surface opposing articulating bone, the partially cured preformed component can be provided with suitable means as well, intended to improve or alter either its compliance and/or interactions with the opposing bone surface.

In one particularly preferred embodiment, the system includes a partially cured preformed component that is first molded outside of the joint site and adapted to be delivered to a tissue site and there positioned in a fixed position. The mold can be of an open or closed configuration (and/or can involve a one- or multi-step molding process), adapted to preform one or both major surfaces, respectively. Once positioned, the partially cured component is adapted to be initially fit and positioned within the joint site, and to thereafter become better conformed to the specific dimensions and/or terrain (e.g., anatomic structure) of the joint site in vivo. Optionally, and preferably, the molds are designed to yield components that have optimum adhesion and conformance to the joint sites. The molds may also be heated during the ex vivo partial curing process to optimize component properties or to provide a component that is more formable in vivo.

In an alternative preferred embodiment, the method and system involve the preparation and use of one or more fully or partially cured component(s) formed outside the body, for insertion and placement into the body and optionally further fitting and securing at the joint site. In one embodiment, the invention provides a single preformed component that is inserted into the joint site and optionally further fitted or secured as needed. In another embodiment, the invention provides a plurality of preformed components, formed of the same or different materials, and adapted to be delivered and positioned at the tissue site in a manner that provides a final composite. The components can be combined at the site in any suitable fashion, e.g., by providing a mechanical lock and/or by the use of interfacial materials such as adhesive layers. The components can be combined in any suitable fashion, e.g., as layers upon the bone, or as individual side-by-side components adapted to traverse the bone surface when combined. The use of preformed component(s) can require less manipulation at the bedside and allow for alternative methods of terminal sterilization, and final inspection and release at the manufacturing site. The various means of retaining partially cured preformed components, discussed herein, can be adapted to work with fully cured preformed components.

The method and system of this invention can be used for repairing a variety of mammalian joints, including human joints selected from the group consisting of the tibial plateau of the knee, the acetabulum of the hip, the glenoid of the shoulder, the acromion process of the shoulder, the acromioclavicular joint of the shoulder, the distal tibial surface of the ankle, the radial head of the elbow, the distal radius of the forearm, the proximal phalanx surface of the great toe, the proximal metacarpal surface of the thumb, and the trapezium of the wrist.

Those portions or combinations of preformed component(s) that contact the bone surface are preferably adapted to physically conform closely to the prepared bone surface, e.g., to its macroscopic physical contours. Such conformation can be provided or enhanced in any suitable manner, e.g., 1) by providing a partially cured preformed component that is first made in an ex vivo mold and then adapted or modified to conform to the surface (e.g., by further forming in vivo), and/or 2) by use of a preformed balloon or composite mold material that is inserted into the joint site and filled with a flowable biomaterial that cures in vivo so that it conforms with the joint site and/or 3) by the use of fully cured preformed component(s) that has optimum geometry for biomaterial compliance once placed in the joint site and/or 4) by the preparation and use of a suitable (e.g., thin) interface material between bone and preformed component (e.g., adhesive, filler, or cement material), and/or 5) by the use of physical restraining means, such as adhesives, pins, staples screws, sutures or the like that are attached to protrusions in the component itself or to an external means of securing it.

In yet other embodiments, the system of this invention can include the use of materials or markers (e.g., radiopaque) positioned within or upon the implant, to aid in visualization. e.g., using fluoroscopy or other X-ray techniques.

Figure 1B:
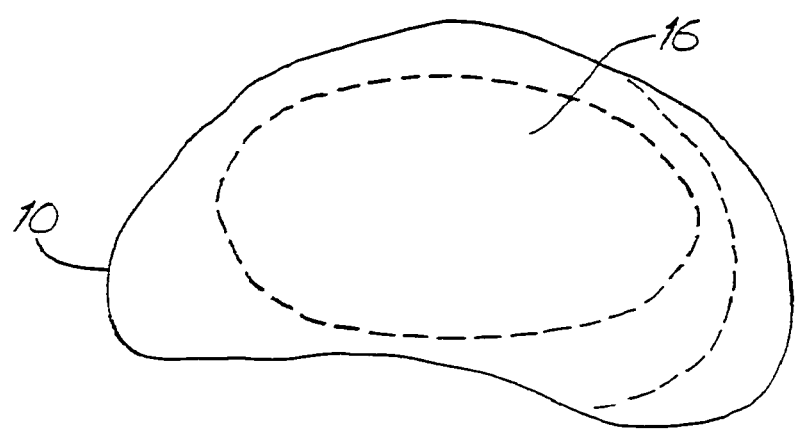

The method and system of this invention will be further described with reference to the Drawing, wherein:

FIG. 1 shows a top and side perspective of a preferred preformed knee implant (10) prepared using an ex vivo mold according to the present invention. The implant provides a first major surface (12) adapted to be positioned upon the tibial surface, and a generally planar second major surface (14) adapted to be positioned against the femoral condyle. In a typical embodiment, the second major surface, in turn, is preferably provided with a femoral glide path (16) to facilitate its performance in situ, in the form of a generally central (e.g., oval) depression about 0.5 mm, or more preferably about 1 mm to about 5 mm deep at its lowest point (2 mm as shown) and about 20 mm, and more preferably about 30 mm to about 50 mm in length by 10 mm to 30 mm in width (40 mm by 20 mm as shown). Those skilled in the art, given the present description, will readily determine the actual dimensions for optimal use, in both absolute and relative terms, depending on such factors as the actual joint size and desired results (e.g., angular correction). As shown, the implant is also provided with a tibial projection (18), adapted to catch the posterior portion of the tibial plateau by extending over the rim of the tibial plateau distally. The body of the implant can have dimensions on the order of between about 35 mm, and preferably about 40 mm to about 60 mm in the anterior-posterior dimension, between about 20 mm, and preferably 30 mm to about 35 mm, or even about 40 mm in the medial-lateral dimension, and a maximum thickness (at the posterior lip of between about 8 mm, more preferably about 10 mm, and about 20 mm, or about 2 mm to about 4 mm (e.g., 3 mm) greater than the thickness of the implant at the center. As a result, it can be seen that fixation is accomplished by effectively capping the tibial plateau with one or more projections extending distally over the rim of the plateau.

Figure 2B:
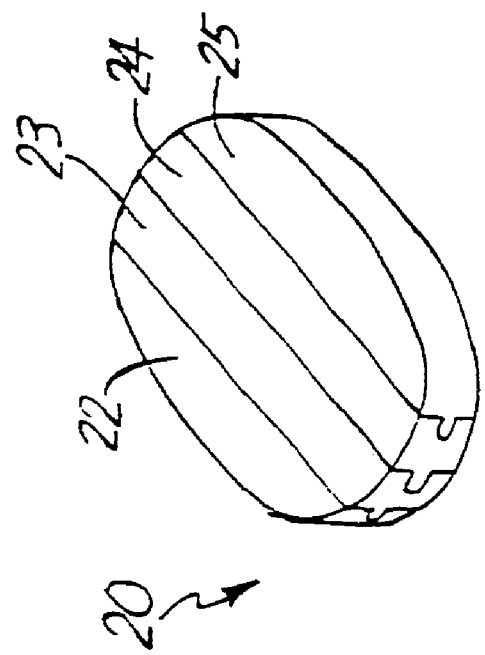
FIG. 2 shows an embodiment, including an in situ view 2a and a raised perspective view 2b, in which preformed components adapted to be inserted and assembled in situ.
Figure 2A:
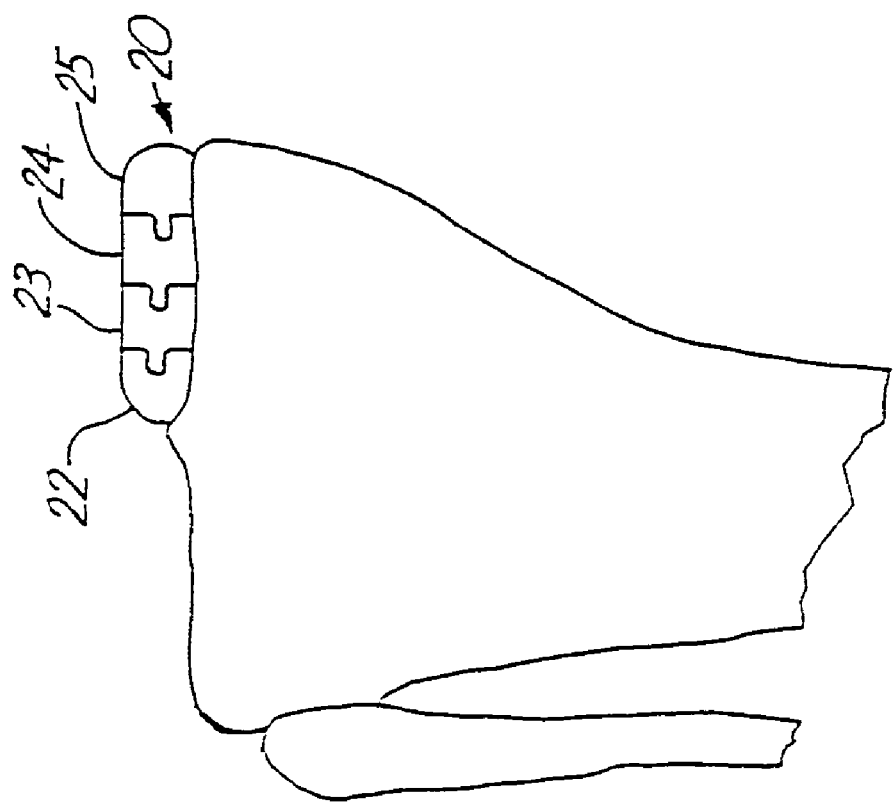

FIG. 2 shows an embodiments in which a plurality of preformed components are adapted to be inserted and assembled in situ to provide the final implant (20) FIG. 2a shows an embodiment, in which preformed components (22 through 25, respectively) are assembled in a side-by-side manner sequentially, and in situ, and upon the tibial surface. The matable preformed sections each provide at least a portion of the resultant bone-contacting surface and wear surface, as well as one or more portions adapted to provide a mechanical lock with one or more respective other portions. The mechanical lock can be achieved in any suitable manner, as by the provision of corresponding male and female portions, respectively. The portions can be mated, in situ, e.g., in a press fit or sliding manner, in order to attach the respective components. As can be seen in the raised perspective of the same embodiment, and FIG. 2b, in the resultant assembly, the combined components cooperate to provide both a tibial bone-contacting surface (28) and a wear surface (26).

Figure 3C:
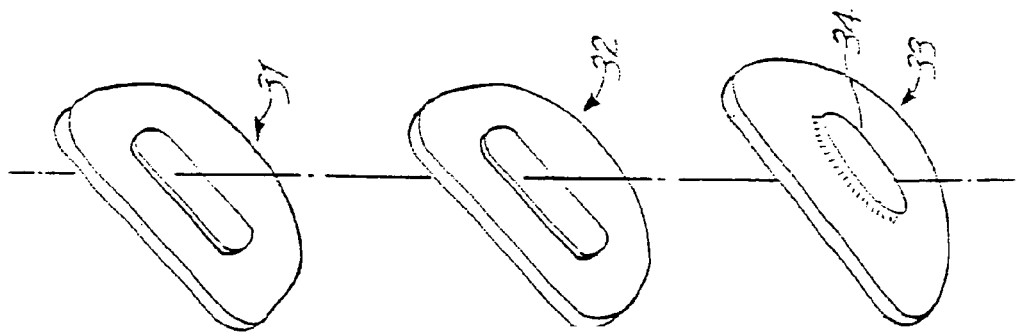
FIGS. 3a, 3b, and 3c shows an alternative embodiment in which preformed components are employed, shown as disassembled components.
Figure 3B:
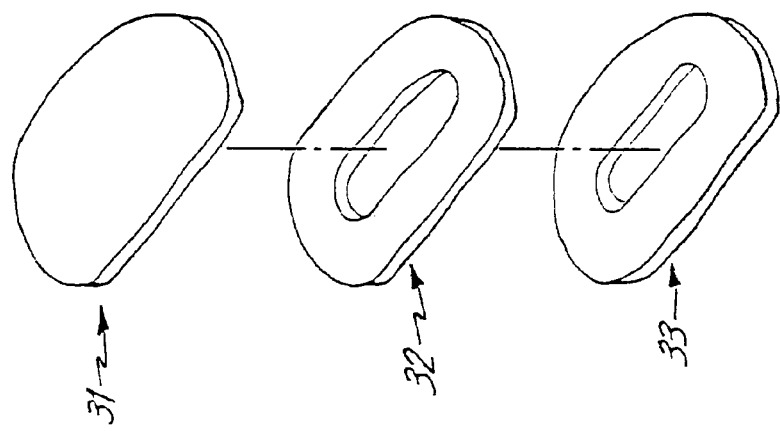
Figure 3A:
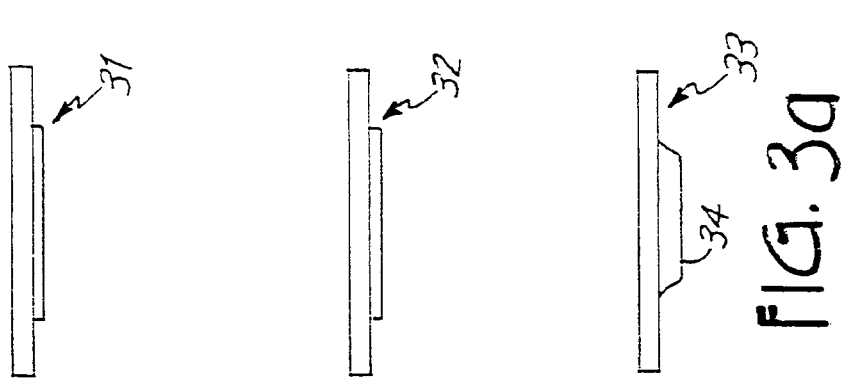

In the alternative embodiment of FIG. 3, rather than being positioned in a side-by-side fashion across the bone surface (as in FIG. 2), a final implant is provided using interlocking preformed components (show in this case as portions 31 through 33, respectively) are instead provided in a form that permits them to be stacked upon each other, e.g., by layering or sliding them onto each other, and positioned upon the surface, in situ. The portions can be assembled in any suitable fashion, e.g., entirely on the tissue site, entirely ex vivo, or in varying combinations as desired. Optionally, and preferably, the generally planar portions are provided with corresponding matable portions, e.g., in the form of grooves and tabs to provide a sliding fit, or a depression and corresponding projection to provide either a press fit, snap fit, or other suitable fit sufficient to prevent lateral displacement to the extent desired. The resultant formed prosthetic implant can be provided with various features as described herein, including desired molded portions adapted to provide better fit or performance. Top portion (31) is particularly well suited to provide a desirable wear surface, while one or more intermediate portions (as shown by element 32) are adapted to provide an optimal combination of such properties as thickness, cushioning, and angular correction. As shown the lowermost portion (33) is shown with a projection (34) adapted to be retained within a corresponding anchor hole or suitable depression formed into the bone itself. FIGS. 3b and 3c provide generally bottom and top views, respectively, showing the manner in which the portions can be combined in a layered fashion.

In the embodiment of FIG. 3, preformed layers are shown having protrusions adapted to be positioned in a corresponding indentation within each underlying layer (or bone), in order to form a compact stack. In such an embodiment, the corresponding system will typically include at least two preformed components, including the initial, bone-contacting component, and final component providing the wear surface. The system can provide one or more intermediate layers, e.g., the number and/or selection of which can be used to provide a final desired height to the overall composite, and/or to provide differing properties (e.g., with respect to compressibility, resilience, tissue ingrowth), and/or to provide improved retention between the first and final components.

Figure 4A:
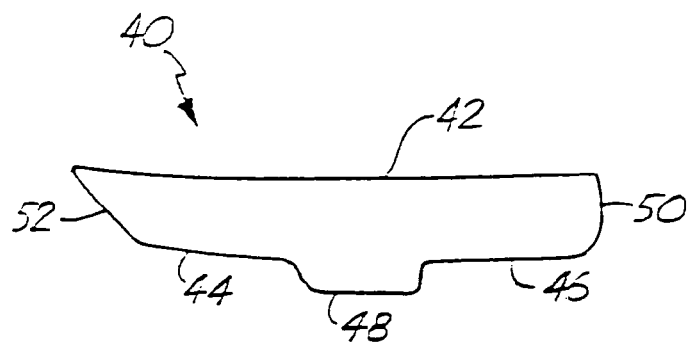
FIGS. 4 and 5 show an embodiment in which a substantially open (saucer-shaped) mold is inserted into the joint site, to be filled with a corresponding curable biomateral in situp including side and bottom perspective views 4a and 4b, respectively, and views showing the mold being positioned (Sa) and being filled while in position upon the knee (Sb).

FIG. 4a shows an embodiment in which a substantially open (saucer-shaped) mold (40) is inserted into the joint site, to be filled with a corresponding curable biomateral in situ. The top (42) of the mold is open to receive biomaterial (not show), while the bottom (44) provides a lower major surface (46) adapted to contact bone and terminates in a filled protrusion (48) adapted to be positioned within a corresponding anchor point drilled in the bone itself. The anterior edge (50) of the cup is substantially perpendicular to the plane of the cup itself, while the posterior edge (52) is tapered (and optionally raised) to accommodate the corresponding shape of the tibial spine.

As shown, and for use in an adult human, the ex vivo mold accommodates a predetermined volume of biomaterial of on the order of about 5 ml to about 15 ml. As a further advantage of this invention, the amount of biomaterial actually can be predetermined and controlled to correspond with the ex vivo mold volume. In addition the ex vivo molds are designed for optimum sizing and conformance to the joint site and MRI software may be used to chose best mold for joint site. Implant thickness and hence angular correction can be controlled in this way.

Figure 4B:
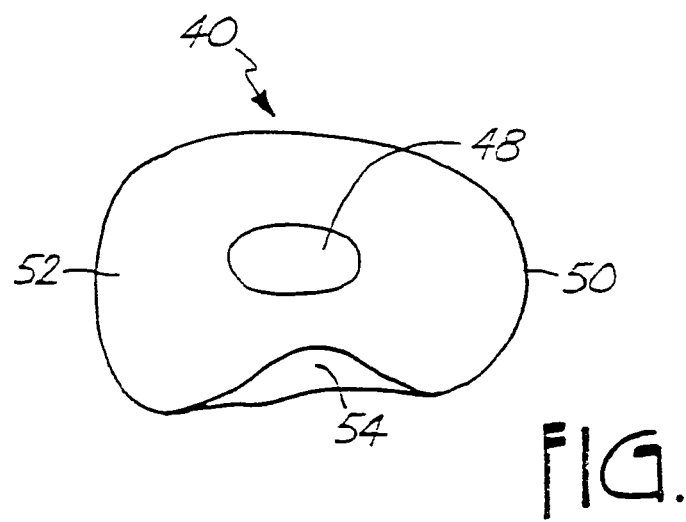

FIG. 4b shows a bottom perspective view of the mold apparatus of FIG. 4a, showing the filled protrusion (48). The posterior edge portion (and particularly the posterior mesial edge portion, as seen in the figure) can be seen as provided with a groove or indentation (54), again to accommodate the typical shape of the corresponding tibial spine. Overall, the mold can be seen as assuming a generally kidney-shaped configuration, adapted to correspond with the tibial surface. Such a mold can be provided in a plurality of sizes, and shapes, to be selected at the time of use to accommodate the particular patient's needs and surgeon's desires.

Figure 5B:
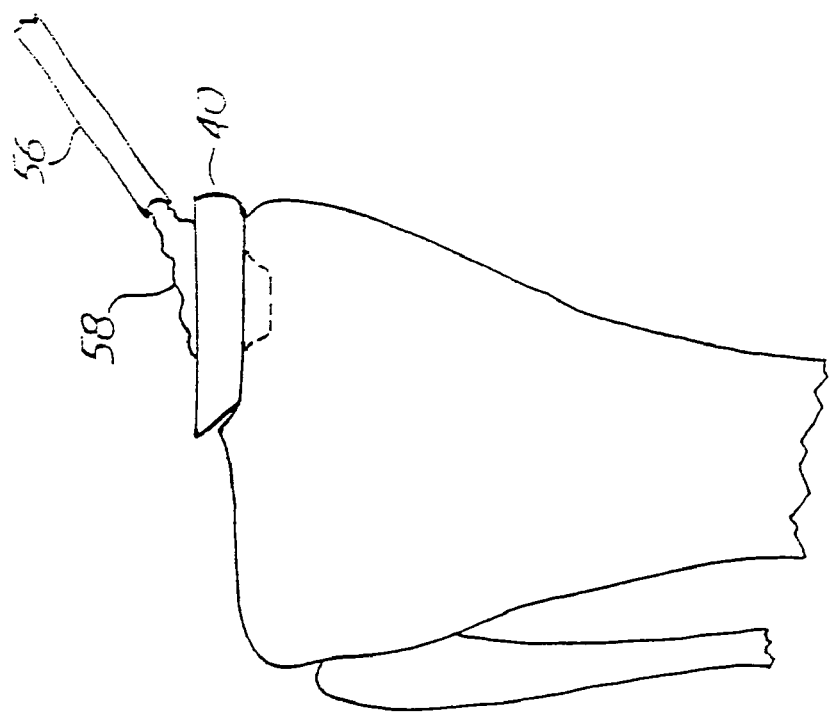
Figure 5A:
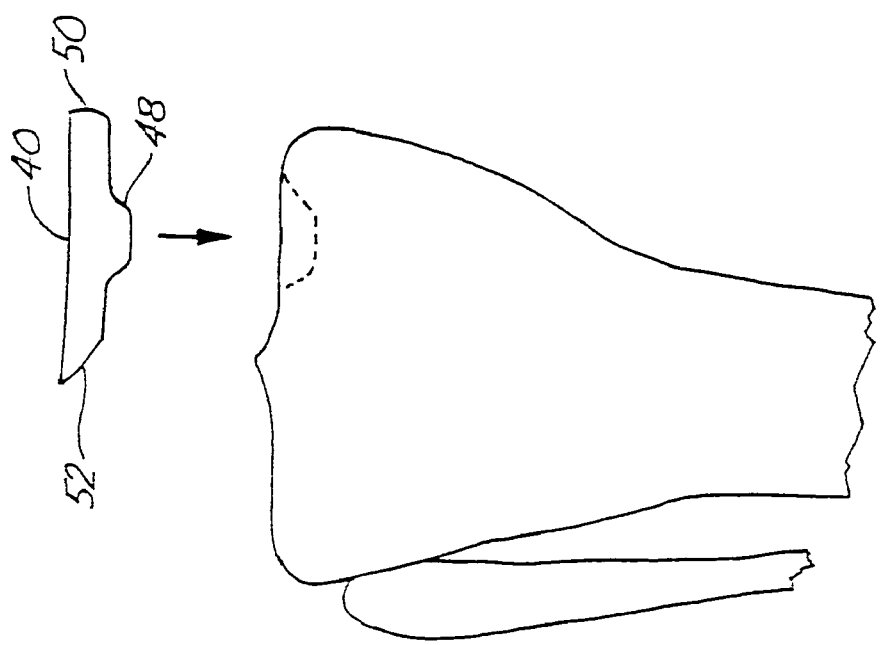

FIGS. 5a and 5b show the mold of FIG. 4a being positioned upon a tibial surface (FIG. 5a), with the protrusion positioned within a corresponding anchor point, and (in FIG. 5b) with the tip of a biomaterial delivery cannula (56) positioned upon it, and with flowable biomaterial (58) being shown in the course of delivery.

FIG. 6 shows a variety of alternative embodiments that include one or more preformed component. FIG. 6a shows a simple wedge shaped embodiment (60), in which the posterior portion (62) is significantly increased in size as compared to the anterior (64). FIG. 6b shows an implant (66) molded to provide portions (here, layers) having differing wear characteristics, including a preformed top having improved wear as compared to the separately formed bottom portion (70). FIG. 6c, by comparison, shows a plurality of components (72) adapted to be positioned and assembled in situ at the time of surgery. These include an upper portion (74) having improved wear characteristics as compared to the others, a bottom portion (78) being suitably formed to the patient's geometry and desired angular correction, and one (or more) central portions (76) adapted to be positioned between the top and bottom portions to achieve desired properties such as overall thickness, angles, and/or physical chemical properties (such as moduli).

Figure 6A:
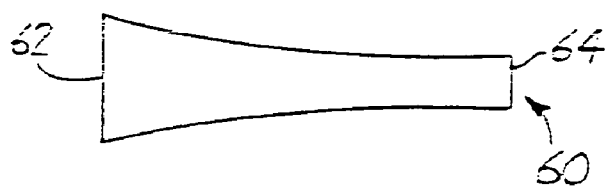
FIG. 6 shows a variety of alternative embodiments 6a, 6b, 6c and 6d, respectively, that include one or more preformed component.
Figure 6B:
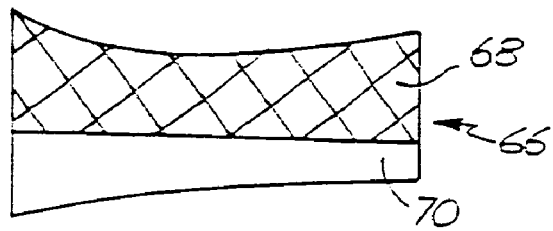
Figure 6C:
Figure 6C:
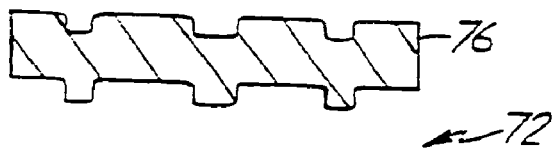
Figure 6C:
Figure 6D:
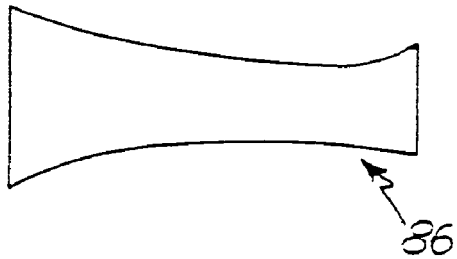
Figure 7A:
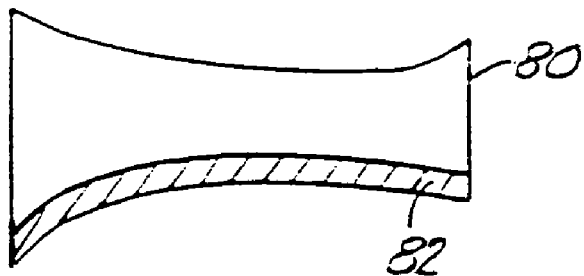
FIG. 7 shows a variety of alternative means 7a, 7b, 7c, and 7d, respectively for anchoring a preformed component such as that shown in FIG. 6d.
Figure 7B:
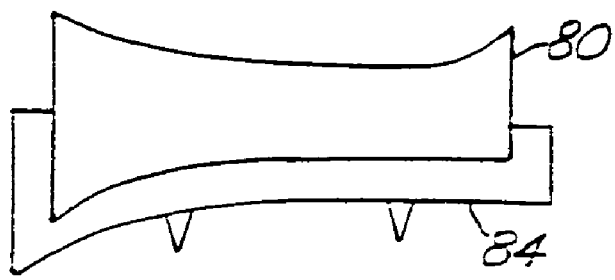
Figure 7C:
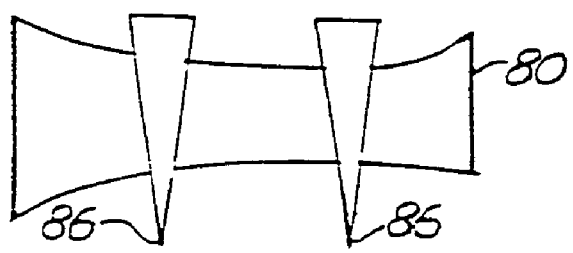
Figure 7D:
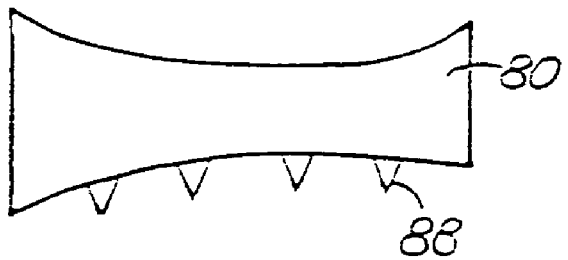

The embodiment of FIG. 6d shows a single piece (80) as might be cut from preformed material at the time of surgery, while FIG. 7 shows a variety of alternative means for anchoring a preformed component such as that shown in FIG. 6d. These include the use of a grout (82) or other suitable interface material as shown in FIG. 7a; the use of a separate external retaining device (84) as shown in FIG. 7b; the use of externally provided pins, screws, sutures, etc. as exemplified by elements (86) which generally traverse the body itself as in FIG. 7c; and the use of one or more anchor portions (88) positioned along one or more suitable surfaces as shown in FIG. 7d.

Figure 8A:
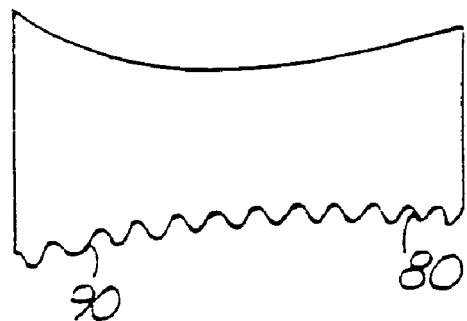
FIG. 8 shows a further variety for anchoring or stabilizing a preformed portion by the use of ancillary portions and/or surface texture, namely embodiments shown as FIGS. 8a, 8b, and 8c.
Figure 8B:
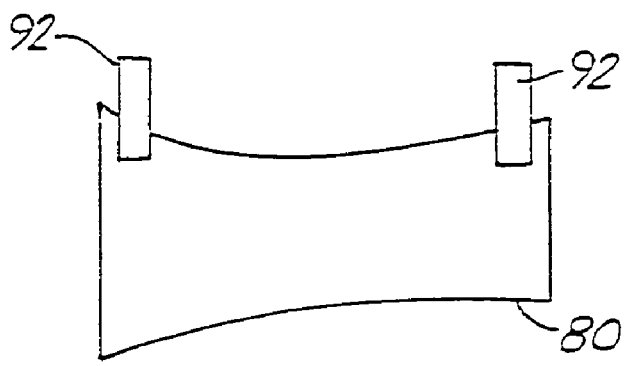
Figure 8C:
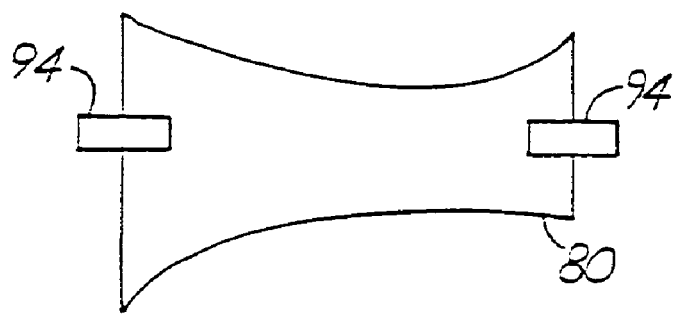

FIG. 8 shows a further variety for anchoring or stabilizing a preformed portion by the use of ancillary portions and/or surface texture, including a roughened surface (90) as in FIG. 8a; or tabs (e.g., provided by fabric or suture like materials) as shown as elements 92 and 94 of FIGS. 8b and 8c, respectively. The surface texture can include, for instance, a dimpled or other suitably textured surface to improve lubricity. In a preferred embodiment, the texture would be sufficient to allow entrapment of lubricant under no load or low loads, followed by obliteration of the pattern with load. In yet another alternative embodiment, a femoral forming device of the type described in Applicant's previous US Provisional Application Ser. No. 0/341,070 can be used to impart a textured surface. In practice, the preformed components can benefit from any suitable combination of the various features and embodiments described or shown herein.

Figure 9A:
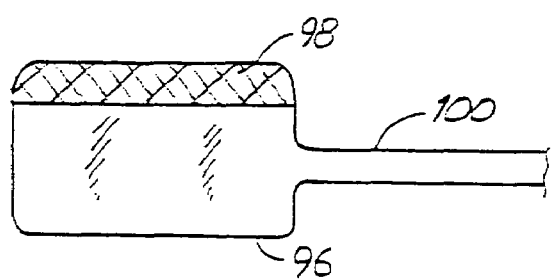
FIG. 9 shows a variety of embodiments, namely those shown as FIGS. 9a, 9b, and 9c, in a substantially closed (balloon like) mold is adapted to be inserted into the joint site and filled with a corresponding curable biomaterial.
Figure 9B:
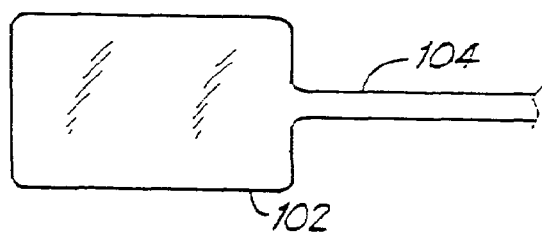
Figure 9C:
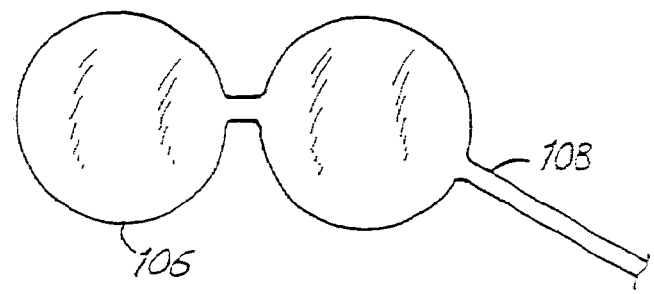

FIG. 9 shows a variety of embodiments in a substantially closed (balloon like) mold is adapted to be inserted into the joint site and filled with a corresponding curable biomaterial, the mold itself providing a preformed articulating wear surface, including FIG. 9a which shows an inflatable balloon portion (96) that includes an integral preformed wear surface and portion (98), as well as a lumen (100) adapted to fill the inflatable portion with flowable biomaterial. FIG. 9b shows a corresponding balloon (102) though without a preformed portion, and including its biomaterial lumen (104). Although not shown, the balloon of this or any embodiment can include various interior and/or exterior surface coatings, and can have regions and/or layers having different desired physical-chemical properties (such as porosity). FIG. 9c shows a bi-compartmental closed balloon-like mold (106), wherein each compartment is adapted to conform to a respective medial or lateral tibial surface.

Figure 10:
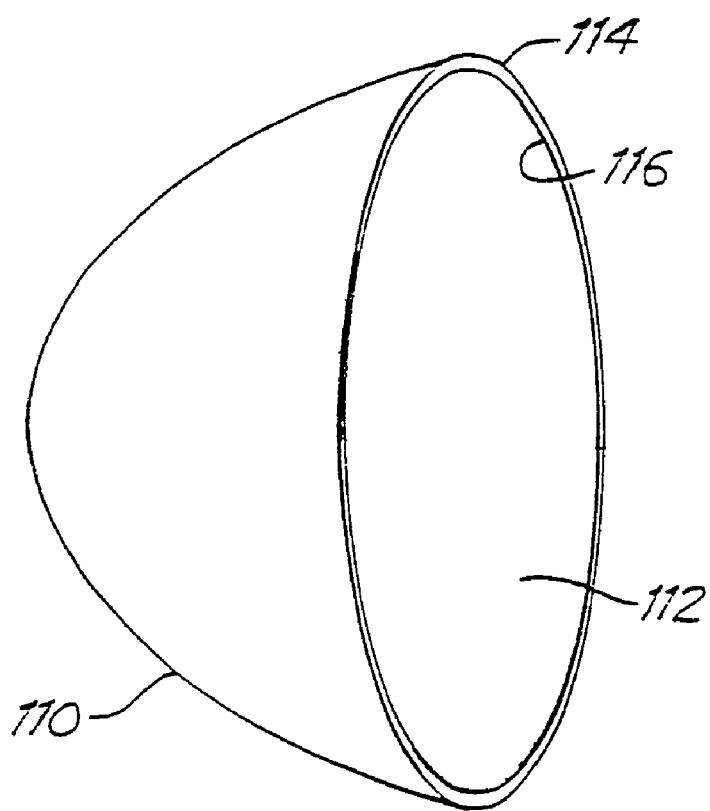
FIG. 10 shows a mold adapted for use as an acetabular mold in connection with the replacement of the articulating surface in a hip.
Figure 11A:
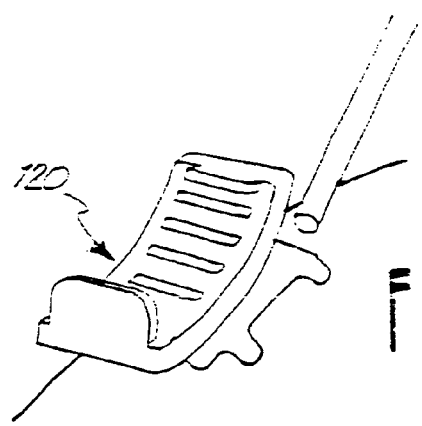
FIG. 11 shows a patella femoral joint form suitable for use in combination with the method and system of this invention, including raised perspective view 11a, top view 11b, side view 11c, and a side view 11d of the form in position upon a condyle.
Figure 11B:
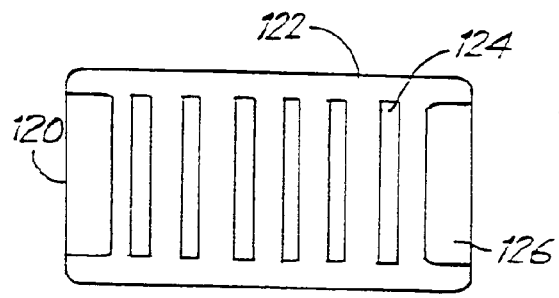
Figure 11C:
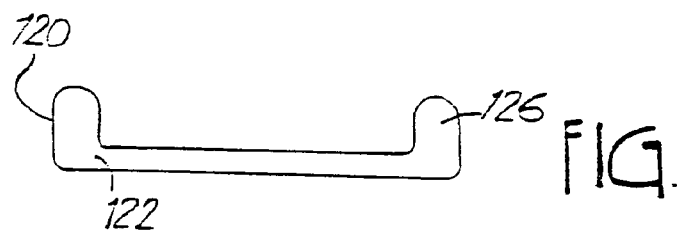
Figure 11D:
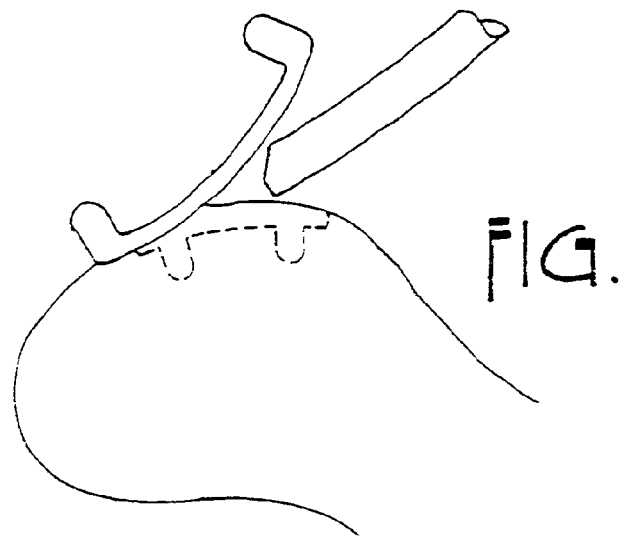

FIG. 10 shows a mold adapted for use as an acetabular mold (110) in connection with the replacement of the articulating surface in a hip, when filled with biomaterial, the mold forming a concave portion adapted to retain a corresponding femoral head. The mold is shown providing a thin generally cup-shaped mold adapted to be filled in any suitable form (e.g., using a removable conduit (not shown) attached to the space between inner and outer sealed layers (116 and 114, respectively) forming the mold.

FIG. 11 shows a patella-femoral joint form suitable for use in combination with the method and system of this invention. As shown in the views of 11a through 11c, the form includes a silicone or other suitable pad material (122) having aluminum or other suitable stay portions (124) and terminal handle or grasping portions (126). In use, with the knee at a generally 45 degree angle, the piece is formed to the femoral bone surface, with its form maintained by bending the aluminum stays. With anchor points cut into the femoral bone, if desired, the form is held tight against the bone with the upper handle held away from bone to permit the delivery of curable biopolymer between the form and the bone. As polymer is placed onto the bone (and into any anchor points) the form is maintained for a time sufficient to suitably form the polymer, whereafter it can be removed.

FIG. 12 shows various views of a particularly preferred implant of the present invention, of the general type shown in FIG. 1 and described above, including a top plan view (a), front plan view (b), side plan view (c), section view (d) taken along A-A of FIG. 12(a) and a section view (e) taken along C-C of FIG. 12(a). FIG. 13, in turn, show side by side top plan views (a) and (b) of corresponding implants for the left and right knees, respectively. Reference numbers for the various portions correspond to those described in FIG. 1, including preformed knee implant (10), the first major surface (12) adapted to be positioned upon the tibial surface, and a generally planar second major surface (14) adapted to be positioned against the femoral condyle. The second major surface is shown having a femoral glide path surface (16) to facilitate its performance in situ, adapted to form a generally central depression having the dimensions described herein. The glide path is fully formed in situ, by a suitable combination of both shaping and repositioning of the femoral condyle in the manner described herein.

An implant of the type shown provides various benefits, including the correction of varus deformities, based in significant part upon the presence and configuration of the posterior mesial lip (18), and the cutout (kidney bean shaped) for the intercondylar eminence (see FIG. 4b, ref 54). The tibial projection (18) is adapted to catch the posterior portion of the tibial plateau. The implant itself has dimensions as provided herein, and can be provided using one of a collection of molds of multiple sizes and/or styles in accordance with the various parameters of the present invention. A kit can be provided containing molds of various sizes, e.g., varying by 1 mm or 2 mm increments in thickness and providing a range of anterior to posterior dimensions. Such molds can also be used to provide implants having bottoms of various shapes, e.g., either a flat or curved bottom, and for either the left or right knee.

An implant such as the configuration shown in FIG. 12 is preferably used in a method that includes first determining the proper implant thickness needed to match physiological valgus. The surgeon prepares the site arthroscopically, removing excess cartilage and removing the medial meniscus to the medial ring, using a portal of about 1cm in order to provide suitable arthroscopic access while maintaining the presence of fluid in the joint. The implant can be initially molded ex vivo, using a mold selected from those available and including one or more embedded or attached fixation portions (e.g., anterior sutures or tabs), at which time it is inserted into the knee. The surgeon will then typically feel the implant once in position, to confirm that the implant is properly seated, and will extend the knee to provide varus stress on the lower leg, obtaining congruency as the implant continues to cure by finally molding both surfaces of the implant (to both the tibial surface and condyle, respectively).

Optionally, and preferably, the surgeon can also use a femoral forming device (e.g., spoon-shaped device) of the type described in copending US Provisional Application mailed Dec. 7, 2001 and entitled "Method and Device for Smoothing The Surface of Bone in an Articulating Joint", the disclosure of which is incorporated herein by reference, in order to prepare a femoral glide path and remove unwanted undulations. After a suitable time, e.g., about 1 to about 5 minutes, and typically at about 2 minutes using presently preferred polyurethane compositions, the implant can be sutured to the anterior rim, and the knee can be flexed to obtain complete range. Optionally, during or following this procedure, the joint can be filled with a suitable fluid and visualized, after which the knee is extended and braced, with the access portal(s) closed by suitable means (e.g., sutured).

As described in Applicant's co-pending U.S. provisional application 60/228,444, the present application describes a method and system for the creation or modification of the wear surface using an implanted material fixed to the support structure of the original wear surface, to generally conform to the shape of the original surface in a mammal. A method or system where the end of the bony surface is a rotating, sliding or rolling surface, such as in the knee, finger, hip, toe, spine, wrist, elbow, shoulder, ankle, or TMJ joint. The implant will function:

a) as a spacer,
b) as an impact absorber
c) as a surface with improved coefficient of friction (as compared to the diseased surface), and/or
d) to increase the weight bearing area and improve congruency of the joint surface (as compared to the diseased condition).

The method and system of this invention can be applied to areas of aseptic necrosis, such as the nevecular bone in the wrist. The material to be implanted consists of a plurality of materials, such as polymers, including polyurethane, polyethyelenes, polyureas, polyacrylates, polyurethane acrylates, hydrogels, epoxies and/or hybrids of any of the above.

In an alternative embodiment, the surface can be provided by any of a series of metals, including titanium, stainless steel, cobalt chrome millithium alloys and tantalum. Other surface materials can include various ceramics and biologic polymers.

The implantable material for the resurfacing can be formed ex vivo and/or in vivo as an injectable material that sets up to the molded shape. The methods for changing state from liquid to solid state include cooling or heating, the passage of time, which allows for a change of state, or a chemical reaction between different reactants. The reaction can be exothermic or endothermic. The set-up can be light activated or chemically catalyzed or it could be heat activated. Examples of such systems include flowable polymers of two or more components, light activated polymers, and polymers cured either by catalysts or by heat, including body heat, or any suitable combination thereof. Molds can be used in the form of balloons, dams or retainers. They can be used in combination with the local anatomy to produce the desired shape and geometry. Molds can be of materials that are retained and becomes part of the implant or could be removed after curing of the biomaterial component.

In an alternative embodiment, the material would be semi-solid and could be shaped and then set up in vivo. This would allow for the minimally invasive application, either through an arthroscopic portal or through a small mini arthrotomy. As a further embodiment, the material could be synthesized ex vivo and then machined to fit using imaging to pre-determine the desired geometry and size of the implant. As a further alternative, a range of implant sizes could be provided and sizing could be accomplished during the procedure. An ex vivo mold could be fit using molding materials and the implant could be molded on site just prior to implantation.

Fixation methods for the implant would include biologic glues to glue the implant to the underlying surface, trapping of the implant into a cavity on the surface that causes a mechanical lock, using various anchors to the underlying structure and fixing the implant to that surface or using mold retainers and/or screws, staples, sutures or pins. In alternative embodiment, anchors in the underlying structure may be used for fixing the implant to that surface and we may also use a tissue ingrowth system to secure anchoring.

In the preferred embodiment, the patient will have a diagnosis of osteoarthritis and have loss of cartilage on the articulating surface. A determination will be made of the amount of correction needed for the reestablishment of a normal angle of articulation. The ligaments will be balanced so that there is no loss of range of motion with the implant in place and the surface will be placed in such a position that the eventual resulting surface geometry reestablishes the same plane and orientation of the original articular surface.

Access to the site is obtained in a minimally invasive way. In a preferred embodiment, this is accomplished through arthroscopic means with arthroscopic portals. In an alternative embodiment, the access is accomplished by a mini arthrotomy with a small incision that allows access to the joint without sacrificing nerves, vessels, muscles or ligaments surrounding the joint. In the preferred embodiment fibrillated articulating cartilage that is degenerated is removed down to the subchondral surface. The surface is dried and prepared for appropriate anchoring. This may include anchor points that give a mechanical lock or that alternatively simply supply horizontal and lateral stability. The surface may be prepared by drying and roughening in case a tissue adhesive is used. Pre-made anchors may be installed. These may be made of various metallic materials or of polymers and may consist of pegs that would extend up through the implant to anchor it to the underlying surface. This surrounding subchondral bone may be roughened to enhance tissue ingrowth or implant adhesion. The final geometry of the implant may be determined by a dam or mold that is placed on the joint at the time the material is implanted, when the implant is installed using an in situ cured technique (in the manner shown in FIGS. 1 and 4 of Applicant's provisional parent application).

For pre-made material formed at the surgical site within a mold, various forms of stabilization could be used, including anchor points or titanium screws. Alternatively, the pre-made material could be made off site to the specs developed from imaging of the patient's joint surface. In a third embodiment, multiple sizes could be made off site and the selection of the appropriate implant size could be chosen at the time of surgery. Two alternatives shown in FIG. 2 of the parent provisional application include a single segment that can be installed through a portal or a series of segments that can be installed through a portal and locked together once inside the joint. They would be placed sequentially and then anchored to the bone by anchor points cut in the bone or by screws or tissue ingrowth. Finally, a robot, a jag or other cutting fixture could be used to prepare the bony surface for the pre-made implant to a fixed geometry of the anchor point.

Both the preformed component(s) and flowable biomaterial, if used, can be prepared from any suitable material. Typically, the materials include polymeric materials, having an optimal combination of such properties as biocompatibility, physical strength and durability, and compatibility with other components (and/or biomaterials) used in the assembly of a final composite. Examples of suitable materials for use in preparing the preformed component(s) may be the same or different from the in situ curing biomaterial, and include polyurethanes, polyethylenes, polypropylenes, Dacrons, polyureas, hydrogels, metals, ceramics, epoxies, polysiloxanes, polyacrylates, as well as biopolymers, such as collagen or collagen-based materials or the like and combinations thereof.

Examples of suitable materials for use in preparing the flowable biomaterial, if used, include polyurethanes, polyureas, hydrogels, epoxies, polysiloxanes, polyacrylates, and combinations thereof.

In a presently preferred embodiment, the preformed component(s) and the flowable biomaterial, if included, each comprise a biocompatible polyurethane. The same or different polyurethane formulations can be used to form both the preformed component(s), e.g., by an injection molding technique, as well as for the flowable biomaterial, if present.

Suitable polyurethanes for use as either the preformed component or biomaterial can be prepared by combining: (1) a quasi-prepolymer component comprising the reaction product of one or more polyols, and one or more diisocyanates, and optionally, one or more hydrophobic additives, and (2) a curative component comprising one or more polyols, one or more chain extenders, one or more catalysts, and optionally, other ingredients such as an antioxidant, and hydrophobic additive.

In the embodiment in which an in situ curing polymer is used, the present invention preferably provides a biomaterial in the form of a curable polyurethane composition comprising a plurality of parts capable of being mixed at the time of use in order to provide a flowable composition and initiate cure, the parts including: (1) a quasi-prepolymer component comprising the reaction product of one or more polyols, and one or more diisocyanates, optionally, one or more hydrophobic additives, and (2) a curative component comprising one or more polyols, one or more chain extenders, one or more catalysts, and optionally, other ingredients such as an antioxidant, hydrophobic additive and dye. Upon mixing, the composition is sufficiently flowable to permit it to be delivered to the body, and there be fully cured under physiological conditions. Preferably, the component parts are themselves flowable, or can be rendered flowable, in order to facilitate their mixing and use.

The flowable biomaterial used in this invention preferably includes polyurethane prepolymer components that react either ex vivo or in situ to form solid polyurethane ("PU"). The formed PU, in turn, includes both hard and soft segments. The hard segments are typically comprised of stiffer oligourethane units formed from diisocyanate and chain extender, while the soft segments are typically comprised of one or more flexible polyol units. These two types of segments will generally phase separate to form hard and soft segment domains, since they tend to be incompatible with one another. Those skilled in the relevant art, given the present teaching, will appreciate the manner in which the relative amounts of the hard and soft segments in the formed polyurethane, as well as the degree of phase segregation, can have a significant impact on the final physical and mechanical properties of the polymer. Those skilled in the art will, in turn, appreciate the manner in which such polymer compositions can be manipulated to produce cured and curing polymers with desired combination of properties within the scope of this invention.

The hard segments of the polymer can be formed by a reaction between the diisocyanate or multifunctional isocyanate and chain extender. Some examples of suitable isocyanates for preparation of the hard segment of this invention include aromatic diisocyanates and their polymeric form or mixtures of isomers or combinations thereof, such as toluene diisocyanates, naphthalene diisocyanates, phenylene diisocyanates, xylylene diisocyanates, and diphenylmethane diisocyanates, and other aromatic polyisocyanates known in the art. Other examples of suitable polyisocyanates for preparation of the hard segment of this invention include aliphatic and cycloaliphatic isocyanates and their polymers or mixtures or combinations thereof, such as cyclohexane diisocyanates, cyclohexyl-bis methylene diisocyanates, isophorone diisocyanates and hexamethylene diisocyanates and other aliphatic polyisocyanates. Combinations of aromatic and aliphatic or arylakyl diisocyanates can also be used.

The isocyanate component can be provided in any suitable form, examples of which include 2,4'-diphenylmethane diisocyanate, 4,4'-diphenylmethane diisocyanate, and mixtures or combinations of these isomers, optionally together with small quantities of 2,2'-diphenylmethane diisocyanate (typical of commercially available diphenylmethane diisocyanates). Other examples include aromatic polyisocyanates and their mixtures or combinations, such as are derived from phosgenation of the condensation product of aniline and formaldehyde. It is suitable to use an isocyanate that has low volatility, such as diphenylmethane diisocyanate, rather than more volatile materials such as toluene diisocyanate. An example of a particularly suitable isocyanate component is the 4,4'-diphenylmethane diisocyanate ("MDI"). Alternatively, it can be provided in liquid form as a combination of 2,2'-, 2,4'- and 4,4'-isomers of MDI. In a preferred embodiment, the isocyanate is MDI and even more preferably 4,4'-diphenylmethane diisocyanate.

Some examples of chain extenders for preparation of the hard segment of this invention include, but are not limited, to short chain diols or triols and their mixtures or combinations thereof, such as 1,4-butane diol, 2-methyl-1,3-propane diol, 1,3-propane-diol ethylene glycol, diethylene glycol, glycerol, cyclohexane dimethanol, triethanol amine, and methyldiethanol amine. Other examples of chain extenders for preparation of the hard segment of this invention include, but are not limited to, short chain diamines and their mixtures or combinations thereof, such as dianiline, toluene diamine, cyclohexyl diamine, and other short chain diamines known in the art.

The soft segment consists of urethane terminated polyol moieties, which are formed by a reaction between the polyisocyanate or diisocyanate or polymeric diisocyanate and polyol. Examples of suitable diisocyanates are denoted above. Some examples of polyols for preparation of the soft segment of this invention include but are not limited to polyalkylene oxide ethers derived form the condensation of alkylene oxides (e.g. ethylene oxide, propylene oxide, and blends thereof), as well as tetrahyrofuran based polytetramethylene ether glycols, polycaprolactone diols, polycarbonate diols and polyester diols and combinations thereof. In a preferred embodiment, the polyols are polytetrahydrofuran polyols ("PTHF"), also known as polytetramethylene oxide ("PTMO") or polytetramethylene ether glycols ("PTMEG"). Even more preferably, the use of two or more of PTMO diols with different molecular weights selected from the commercially available group consisting of 250, 650, 1000, 1400, 1800, 2000 and 2900. Two or more PTMO diols of different molecular weight can be used as a blend or separately, and in an independent fashion as between the different parts of the two part system. The solidification temperature(s) of PTMO diols is generally proportional to their molecular weights. The compatibility of the PTMO diols with such chain extenders as 1,4-butanediol is generally in the reverse proportion to molecular weight of the diol(s). Therefore the incorporation of the low molecular weight PTMO diols in the "curative" (part B) component, and higher molecular weight PTMO diols in the prepolymer (part A) component, can provide a two-part system that can be used at relatively low temperature. In turn, good compatibility of the low molecular weight PTMO diols with such chain extenders as 1,4-butanediol permits the preparation of two part systems with higher (prepolymer to curative) volume ratio. Amine terminated polyethers and/or polycarbonate-based diols can also be used for building of the soft segment.

The PU can be chemically crosslinked, e.g., by the addition of multifunctional or branched OH-terminated crosslinking agents or chain extenders, or multifunctional isocyanates. Some examples of suitable crosslinking agents include, but are not limited to, trimethylol propane ("TMP"), glycerol, hydroxyl terminated polybutadienes, hydroxyl terminated polybutadienes (HOPB), trimer alcohols, Castor oil polyethyleneoxide (PEO), polypropyleneoxide (PPO) and PEO-PPO triols. In a preferred embodiment, HOPB is used as the crosslinking agent.

This chemical crosslinking augments the physical or "virtual" crosslinking of the polymer by hard segment domains that are in the glassy state at the temperature of the application. The optimal level of chemical cross-linking improves the compression set of the material, reduces the amount of the extractable components, and improves the biodurability of the PU. This can be particularly useful in relatively soft polyurethanes, such as those suitable for the repair of damaged cartilage. Reinforcement by virtual crosslinks alone may not generate sufficient strength for in vivo performance in certain applications. Additional cross-linking from the soft segment, potentially generated by the use of higher functional polyols can be used to provide stiffer and less elastomeric materials. In this manner a balancing of hard and soft segments, and their relative contributions to overall properties can be achieved.

Additionally, a polymer system of the present invention preferably contains at least one or more, biocompatible catalysts that can assist in controlling the curing process, including the following periods: (1) the induction period, and (2) the curing period of the biomaterial. Together these two periods, including their absolute and relative lengths, and the rate of acceleration or cure within each period, determines the cure kinetics or profile for the composition. Some examples of suitable catalysts for preparation of the formed PU of this invention include, but are not limited to, tin and tertiary amine compounds or combinations thereof such as dibutyl tin dilaurate, and tin or mixed tin catalysts including those available under the tradenames "Cotin 222", "Formrez UL-22" (Witco), "dabco" (a triethylene diamine from Sigma-Aldrich), stannous octanoate, trimethyl amine, and triethyl amine. In a preferred embodiment, the catalyst is Formrez UL-22 (Witco). In an alternative preferred embodiment, the catalyst is a combination Cotin 222 (CasChem) and dabco (Sigma-Aldrich).

The in vivo and ex vivo cured polyurethanes of this invention can be formed by the reaction of two parts. Part I of which (alternatively referred to as Part A) includes a di- or multifunctional isocyanate or quasi-prepolymer which is the reaction product of one or more OH-terminated components, and one or more isocyanates. Part II of the polyurethane (alternatively referred to as Part B herein) is a curative component that includes of one or more chain extenders and one or more polyols, and one or more catalysts, and other additives such as antioxidants and dyes. For a suitable formed PU, the stoichiometry between Parts I (quasi-prepolymer) and II (curative component), expressed in terms of NCO:OH molar ratio of the isocyanate terminated prepolymer (Part I) and the curative component (Part II) is preferably within the range of about 0.8 to 1.0 to 1.2 to 1.0, and more preferably from about 0.9 to 1 to about 1.1 to 1.0.

Optionally, a reactive polymer additive can be included and is selected from the group consisting of hydroxyl- or amine-terminated compounds selected from the group consisting of poybutadiene, polyisoprene, polyisobutylene, silicones, polyethylene-propylenediene, copolymers of butadiene with acryolnitrile, copolymers of butadiene with styrene, copolymers of isoprene with acrylonitrile, copolymers of isoprene with styrene, and mixtures of the above.

Suitable compositions for use in the present invention are those polymeric materials that provide an optimal combination of properties relating to their manufacture, application, and in vivo use. In the uncured state, such properties include component miscibility or compatibility, processability, and the ability to be adequately sterilized or aseptically processed and stored. In the course of applying such compositions, suitable materials exhibit an optimal combination of such properties as flowability, moldability, and in vivo curability. In the cured state, suitable compositions exhibit an optimal combination of such properties as strength (e.g., tensile and compressive), modulus, biocompatibility and biostability.

When cured, the compositions demonstrate an optimal combination of properties, particularly in terms of their conformational stability and retention of physical shape, dissolution stability, biocompatibility, and physical performance, as well mechanical properties such as load-bearing strength, tensile strength, shear strength, shear fatigue resistance, impact absorption, wear resistance, and surface abrasion resistance. Such performance can be evaluated using procedures commonly accepted for the evaluation of natural tissue and joints, as well as the evaluation of materials and polymers in general. In particular, a preferred composition, in its cured form, exhibits mechanical properties that approximate or exceed those of the natural tissue it is intended to provide or replace.

To achieve these desirable uncured and delivery properties, a "polymer system", as used herein refers to the component or components used to prepare a polymeric composition of the present invention. In a preferred embodiment, a polymer system comprises the components necessary to form two parts: Part I being an NCO terminated pre-polymer (optionally referred to as an "isocyanate quasi-polymer"). The quasi-polymer of Part I typically includes a polyol component, optionally in combination with a hydrophobic additive component, and an excess of an isocyanate component. Part II of the two component system can include one long-chain polyols, chain extenders and/or cross-linkers, together with other ingredients (e.g., catalysts, stabilizers, plasticizers, antioxidants, dyes and the like). Such adjuvants or ingredients can be added to or combined with any other component thereof either prior to or at the time of mixing, delivery, and/or curing.

In a particularly preferred embodiment, a polymer system of this invention is provided as a plurality of component parts and employs one or more catalysts. The component parts, including catalyst, can be mixed to initiate cure, and then delivered, set and fully cured under conditions (e.g., time and exotherm) sufficient for its desired purpose. Upon the completion of cure, the resultant composition provides an optimal combination of properties for use in repairing or replacing injured or damaged tissue. In a particularly preferred embodiment, the formulation provides an optimal combination of such properties as compatibility and stability of the biomaterial parts, ex vivo or in situ cure capability and characteristics (e.g., extractable levels, biocompatibility, thermal/mechanical properties), mechanical properties (e.g., tensile, tear and fatigue properties), and biostability.

The volume ratio of the parts can also be used to improve and affect the uncured and curing properties Compositions having two or more parts, are preferred. Where two parts are used, the relative volumes can range, for instance, from 1:10 to 10:1 (quasi-prepolymer to curative components, based on volume). A presently preferred range is between 2:1 and 1:2. As those skilled in the art will appreciate, given the present description, the optimal volume ratio is largely determined by the compatibility and the stability of part A and B.

In choosing an optimal volume ratio for a given formulation, those skilled in the art, given the present description, will appreciate the manner in which the following considerations can be addressed. The viscosity of the reactive parts, at the temperature used for either injection-molding preformed components, or for in situ cure, should provide an acceptable degree of mixing and flow rate, without causing mechanical failure of any component of the delivery system including cartridge, static mixer, gun and other components.

Preferably, the biomaterial is sufficiently flowable to permit it to be delivered (e.g., injected) into the mold or tissue site. The composition of both reactive parts must be such that these parts are homogeneous and phase stable in the temperature range of the application. Generally, the maximum temperature of the reaction exotherm is proportional to the concentration of the reactive groups in the mixed polymer. A high concentration of the reactive groups might evolve too high reaction exothermal energy and therefore cause thermal damage to the surrounding tissues. The reactive parts will preferably remain substantially liquid in form during mixing.

A desired and stable volume ratio of the components can be achieved in any suitable manner, e.g., by the use of dual-compartment cartridges with constant volume ratio or by using the injectors with delivery rates independently variable for each component.

Compatibility of the composition can also be affected (and improved) in other ways as well, e.g., by pre-heating the components prior to polymer application. To enhance the homogeneity of the components, the components of a preferred composition of this invention are preferably preheated before mixing and delivery, e.g., by heating to about 40 C, more preferably about 60 C, to about 80 C for about 2 to about 6 hours prior to use or for the time necessary for complete melting and forming of the member. Preferably, the composition parts are cooled back to about 35 C to 37 C before use in injection.

Fully cured polymeric (e.g., polyurethane) biomaterials suitable for use in forming components of this invention provide an optimal combination of such properties as creep and abrasion resistance. Preferably, for instance, the biomaterial provides DIN abrasion values of less than about 100 mm, more preferably less than about 80 $mm^3$ and most preferably less than about 60 mm, as determined by ASTM Test Method D5963-96 ("Standard Test Method for Rubber Property Abrasion Resistance Rotary Drum Abrader").

What is claimed is:

1. A system for the modification of a knee, the system comprising a knee implant that provides a first major surface adapted to be positioned upon a tibial plateau, and a second major surface adapted to be positioned against a femoral condyle, the second major surface being provided with a femoral glide path to facilitate its performance in situ, the glide path being in the form of a generally central depression, the implant further comprising one or more tibial projections, extending distally over a rim of the tibial plateau and into a posterior cruciate ligament (PCL) fossa of a tibia, wherein the implant remains substantially permanently anchored in place with respect to the tibial plateau when positioned in the knee by a combination comprising the first major surface, the second major surface, and the tibial projection(s).

2. A system according to claim 1 wherein the glide path is in the form of a generally central depression about 0.5 mm to about 5 mm deep at its lowest point.

3. A system according to claim 1 wherein the glide path is in the form of a generally central depression about 20 mm to about 50 mm in length by 10 mm to 30 mm in width.

4. A system according to claim 1 wherein the glide path is in the form of a generally central oval depression about 0.5 mm to about 5 mm deep at its lowest point.

5. A system according to claim 1 wherein the glide path is in the form of a generally central oval depression about 20 mm to about 50 mm in length by 10 mm to 30 mm in width.

6. A system according to claim 1 wherein the tibial projection(s) are adapted to catch a posterior portion of the tibial plateau by extending over the rim of the tibial plateau distally.

7. A system according to claim 1 wherein the knee implant has dimensions on the order of between about 30 to about 60 mm in the anterior-posterior dimension.

8. A system according to claim 1 wherein the knee implant has dimensions on the order of between about 20 mm to about 40 mm in the medial-lateral dimension.

9. A system according to claim 1 wherein the knee implant has a maximum thickness, at the tibial projection(s), of between about 8 mm and about 20 mm.

10. A system according to claim 1 wherein the knee implant has a maximum thickness, at the tibial projection(s), of about 2 mm to about 10 mm greater than the thickness of the implant at the center.

11. A system according to claim 1 wherein the knee implant has dimensions on the order of between about 30 to about 60 mm in the anterior-posterior dimension, between about 20 mm to about 40 mm in the medial-lateral dimension, and a maximum thickness, at the tibial projection(s), of between about 8 mm and about 20 mm, or about 3 mm to about 10 mm greater than the thickness of the implant at the center.

12. A system according to claim 1 wherein the glide path is in the form of a generally central oval depression about 0.5 mm to about 5 mm deep at its lowest point and about 20 mm to about 50 mm in length by 10 mm to 30 mm in width.

13. A system according to claim 1, the implant providing a replacement for articular cartilage and meniscus to restore alignment of a knee.

14. A system according to claim 1, wherein the first surface is generally convex.

15. A system according to claim 1, wherein the second surface is generally concave.

16. A system according to claim 1, wherein the implant includes a generally kidney shape.

17. A system according to claim 1, wherein the first surface has an indentation to accommodate a tibial spine.

18. A system according to claim 1, the implant having a central portion and a peripheral thickness, the peripheral thickness being generally thinner than the thickness of the central portion.

19. A system according to claim 1, wherein the first surface is generally convex and has an indentation to accommodate a tibial spine, the second surface is generally concave, the implant is generally kidney shaped, the implant having a central portion and a peripheral thickness, the peripheral thickness being generally thinner than the thickness of the central portion.

20. A system according to claim 1 wherein the implant comprises a material selected from the group consisting of polyurethanes, polyethylenes, polypropylenes, Dacrons, polyureas, hydrogels, metals, ceramics, epoxies, polysiloxanes, and polyacrylates.

21. A system according to claim 1 wherein the implant comprises a polymer.

22. A system according to claim 1 wherein the second major surface has a femoral surface shape that serves largely as the glide path with respect to the femoral condyle in order to provide a replacement for the function of articular cartilage as well as meniscus, and particularly at a central weight-bearing area, in order to restore alignment.

23. A system according to claim 22 wherein the first major surface is convex.

24. A system according to claim 23 wherein the implant provides an indentation adapted to accommodate a tibial spine, a slight feathering of the implant on the first major surface at the tibial spine, a general kidney shape, and a convex first major surface, which together permit the implant to be congruent with a tibia.

* * * * *